(12) United States Patent
Porter et al.

(10) Patent No.: US 6,551,495 B1
(45) Date of Patent: Apr. 22, 2003

(54) ELECTROCHEMICAL ASSAYS

(75) Inventors: Robert Andrew Porter, Northamptonshire (GB); Robert Andrew Badley, Bedford (GB)

(73) Assignee: Inverness Medical Switzerland GmbH, Zug (CH)

( * ) Notice: Subject to any disclaimer, the term of this patent is extended or adjusted under 35 U.S.C. 154(b) by 0 days.

(21) Appl. No.: 09/554,765

(22) PCT Filed: Nov. 23, 1998

(86) PCT No.: PCT/GB98/03495
§ 371 (c)(1),
(2), (4) Date: May 19, 2000

(87) PCT Pub. No.: WO99/27356
PCT Pub. Date: Jun. 3, 1999

(30) Foreign Application Priority Data

Nov. 21, 1997 (EP) .............................................. 97309425

(51) Int. Cl.$^7$ ........................................... G01N 27/327
(52) U.S. Cl. ............................. 205/777.5; 204/403.01; 204/403.12; 435/7.1; 436/544; 436/806
(58) Field of Search ........................... 204/403, 403.01, 204/403.12; 205/777.5, 792; 435/4, 7.1; 436/544, 806

(56) References Cited

U.S. PATENT DOCUMENTS

| 5,776,324 A | * | 7/1998 | Usala .......................... 204/403 |
| 5,942,388 A | * | 8/1999 | Willner et al. .................. 435/6 |
| 6,060,327 A | * | 5/2000 | Keen ............................ 436/518 |

FOREIGN PATENT DOCUMENTS

| EP | 0 142 301 A2 | 5/1985 |
| EP | 0 239 969 A2 | 10/1987 |
| WO | WO 95/29199 | 11/1995 |
| WO | WO 97/27474 | 7/1997 |

OTHER PUBLICATIONS

K.Kham et al " Comparaison des proprietes de conduction du 9, 9'–diethyle 3, 3'–dicarbazyle et de poly (3, 6–n alkylcarbazolediyl). II, Syntheses et proprietes du dimere." Journal de Chimie Physique et de Physico–Chimie Biologique, vol. 92, No. 4, Apr. 1995, pp. 823–826, XP002097040.

J. Electroanal.Chem. 132 (1982) 155—161 XP–002097041 " Morphological stabilization of polymer–coated electrodes by electrochemical cross–linking" Frank B. Kaufman et al Month unavailable.

Synthetic Metals 38 ( 1990 ) 331—340 XP–002097042 " Chain length effect on the electroactivity of poly (N–Alkyl–3,6–Carbazolediyl) Thin films " A Stove et al Month unavailable.

Journal of Electroanalytical Chemistry 418 (1996) 67—72 XP–002065198 " Amperometric amplification of anti-gen–antibody–association at monolayer interfaces: design of immunosensor electrodes " eugenii Katz et al Month unavailable.

* cited by examiner

Primary Examiner—Robert J. Warden, Sr.
Assistant Examiner—Kaj K. Olsen
(74) Attorney, Agent, or Firm—Oppedahl & Larson LLP

(57) ABSTRACT

Disclosed is a component for a device for detecting the presence of an analyte of interest in a sample, the component comprising an electrically conducting solid support having immobilized thereon a chemical moiety, said chemical moiety comprising an electroactive portion with an electrochemical property capable of being directly modulated in a detectable manner by the binding thereto of a binding partner having a specific binding activity for the electroactive portion, together with apparatus comprising the component, and a method of detecting the presence of an analyte of interest.

60 Claims, 13 Drawing Sheets

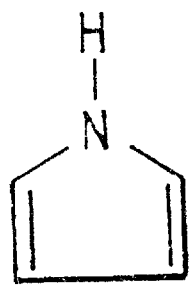 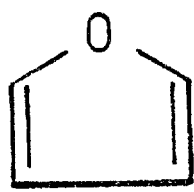 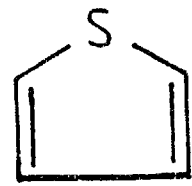
Fig.1(A)  Fig.1(B)  Fig.1(C)
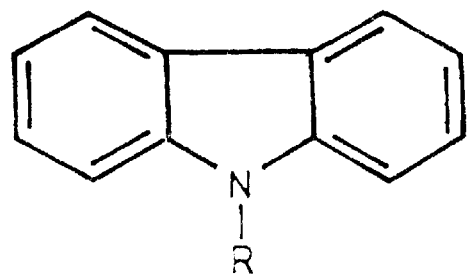
Fig. 1(D)

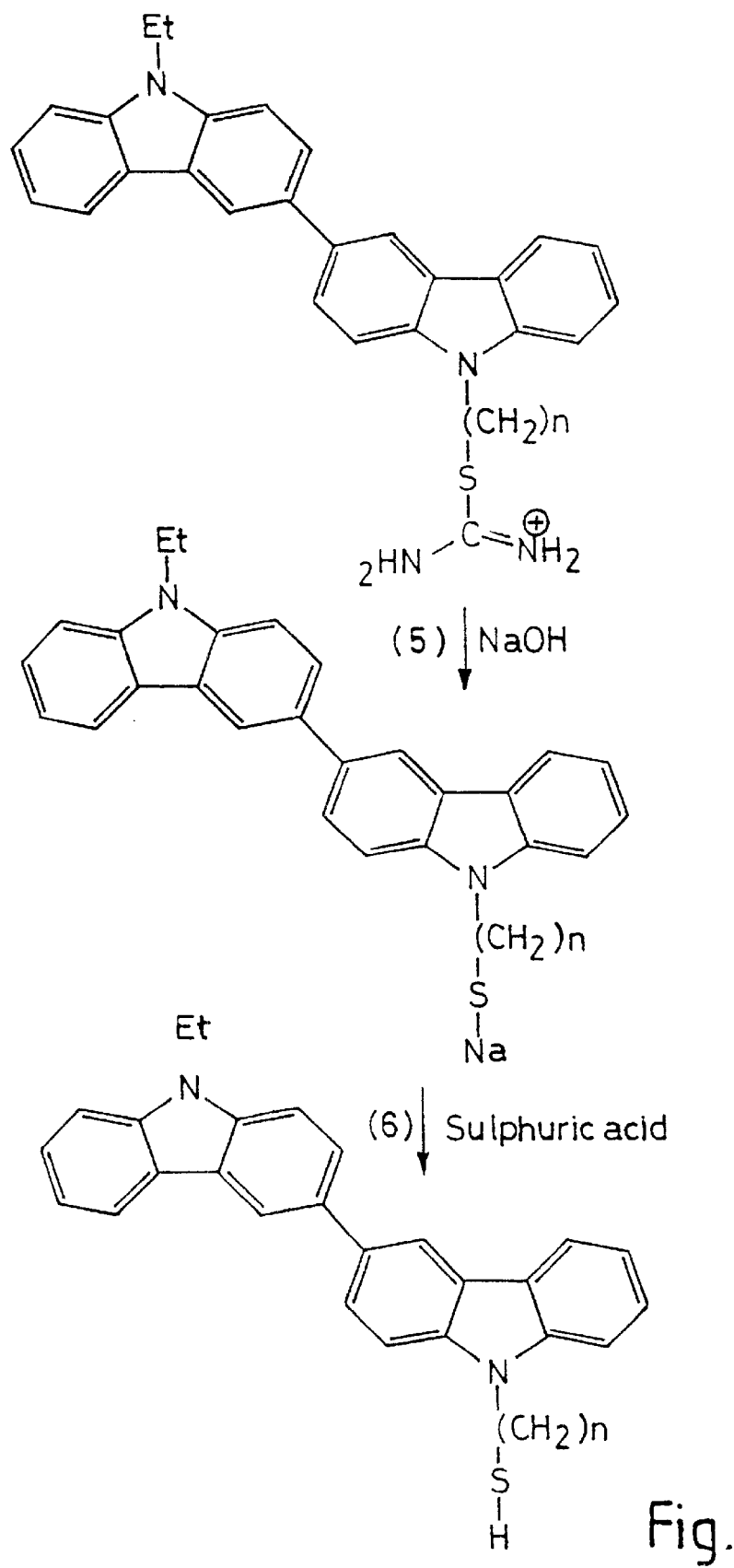
Fig. 6 (contd.)

ELECTROCHEMICAL ASSAYS

FIELD OF THE INVENTION

This invention relates, inter alia, to an assay method and to an assay device.

BACKGROUND OF THE INVENTION

This invention relates in general to electrochemical assays. In such assays, the presence of an analyte of interest in a sample causes a measurable change in an electrochemical property of a sensor device. Typically, electrochemical assays are classified as "potentiometric" or "amperometric", which measure changes in either potential or current respectively.

A number of electrochemical assays have been described. For example, enzyme electrodes have been used for the direct measurement of biomolecules such as glucose, urea, amino acids, and others in physiological samples. These enzyme electrodes include a selective enzyme layer immobilized at the surface of a potentiometric or amperometric device that senses the steady state concentration of a product formed in the immobilized layer as the substrate for the enzyme diffuses into this reactive film.

Other assays involve the use of Nafion™ (E.I. Du Pont de Nemours and Co. Inc.) film. Nafion™ is a polyanionic perfluorosulphonate ionomer with permselective properties large hydrophobic cations rather than small, hydrophilic cations tend to accumulate in the polymer via cationic exchange.

Limoges & Degrand (1993 Analytical Chemistry 65, 1054–1060) described a model system is which a Nafion™-coated electrode was used to detect the presence of amphetamine. The assay took the form of a competitive immunoassay, in which amphetamine in a sample competed with known amounts of labelled amphetamine for binding to amphetamine—specific antibodies. The competitor amphetamine was labelled with cobalticenium, which is a redox label.

The basis for the assay is that once bound by antibody, the labelled amphetamine is excluded from the Nafion™ film because of the large size of the resulting amphetamine/antibody complex. Thus, in the presence of high concentrations of amphetamine in the sample, there is more free labelled amphetamine available for ion exchange and incorporation into the Nafion™ film. Accordingly, the current corresponding to the oxidation or reduction of the cobalticenium-label in the film is proportional to the concentration of amphetamine in the introduced sample.

This sort of assay has several disadvantages and accordingly has not been widely adopted. In particular it requires the performance of a number of reaction steps before detection can effected by the Nafion™-coated electrode. The assay apparatus disclosed by Limoges & Degrand comprised a sensor which was not disposable or re-usable.

A different sort of electrochemical assay involves the use of an "Antibody responsive membrane electrode", as described by Solsky & Rechnitz (1979 Science 204, 1308; 1981 Anal. Chim. Acta 123, 135). The antibody responsive membrane comprised ionophores (crown ethers) within a polyvinyl chloride matrix, the ionophores being conjugated to a hapten in such a way that the haptens projected from the surface of the membrane. The membrane was mounted in the tip of a conventional potentiometric membrane electrode. The addition of a sample containing antibodies specific for the hapten would allow antibodies to bind to the hapten which, in some unknown way, altered the electrochemical properties of the ionophores, changing the potential across the membrane.

The manner in which the device works is not understood, making it impossible rationally to design improvements thereon. Also, the associated detection system is large and cumbersome and not readily re-usable.

WO 89/11649 discloses a device for use in an electrochemical assay, the device comprising an electroactive polymer layer, within which layer are entrapped antibody molecules having binding specificity for an analyte of interest. Binding of the analyte of interest to the antibody inhibits the flow of counter ions from the environment surrounding the device into the space around the electroactive polymer, hence inhibiting electron flow to or from the polymer during a redox reaction. There is no disclosure of the electrochemical properties of the polymer being affected by the binding of a binding partner directly to the polymer.

WO 95/29199 discloses an electrode having a similar arrangement, wherein binding of a binding partner to a chemical moiety attached to an electroactive polymer can indirectly affect the electrochemical properties of the polymer. There is no disclosure of a binding partner having binding specificity for the electroactive polymer itself. A similar arrangement is disclosed in EP 0239969.

WO 93/25907 discloses a competition assay system involving an antigen of interest, and a derivatised antigen carrying a redox label, competing for binding to limiting amounts of antibody. Excess redox-labelled antigen is bound electrostatically to a polymer-coated film, so as to alter the redox potential across the film, which is measured in a conventional manner. The polymeric layer is not electroactive and essentially non-conducting.

EP 0402917 discloses a biosensor operating on a very similar principle to that disclosed in WO 89/11649: a conducting surface with an electroactive surfactant coating is modified by inclusion of one member of a specific binding pair. The analyte of interest is the other member of the specific binding pair. Binding of the reciprocal members of the specific binding pair blocks the movement of counter ions. There is no binding event involving binding directly to the electroactive surfactant.

WO 97/27474 discloses a method of determining the presence of an analyte of interest, whereby an electrode is coated with a member of a specific binding pair. In the absence of analyte of interest (which is the reciprocal member of the specific binding pair), an electroactive redox molecule can come into proximity with the electrode and donate electrons to, or accept electrons from, the electrode. This process is inhibited by the analyte of interest, which blocks the redox molecule from coming into proximity with the electrode. Thus there is no disclosure of the direct binding of a binding partner to an electroactive molecule so as to modify the electrochemical properties thereof. (All documents cited in the present specification are incorporated herein by reference).

The present invention aims to provide an improved type of electrochemical assay, particularly one which will be suitable for forming the basis of disposable, easy-to-use assay devices.

SUMMARY OF THE INVENTION

In a first aspect the invention provides a method of detecting the presence of an analyte of interest in a sample, the method comprising the steps of: providing an electrically conducting solid support having immobilised thereon a chemical moiety having an electroactive portion with an electrochemical property capable of being modulated in a detectable manner directly by the binding thereto of a binding partner having specific binding activity for the electroactive portion; and causing the binding partner to contact the electroactive portion of the chemical moiety as a result of the presence in the sample of the analyte of interest.

In a second aspect, the invention provides a component for a device for detecting the presence of an analyte of interest in a sample, the component comprising an electrically conducting solid support having immobilised thereon a chemical moiety, said chemical moiety comprising an electroactive portion with an electrochemical property capable of being directly modulated in a detectable manner by the binding thereto of a binding partner having specific binding activity for the electroactive portion.

The method of the invention may be used qualitatively, so as to indicate the presence or absence of the analyte of interest. Alternatively, and preferably, the method may be used quantitatively so as to indicate the amount (in relative or absolute units) of the analyte present. It will be apparent that all sorts of substances may be analytes of interest, although biological molecules (i.e. molecules present in or produced by living organisms) will typically be of most interest. These include nucleic acids (DNA and RNA or chimeras thereof, carbohydrates, enzymes, antigens, allergens), hormones (both protein and steroid varieties), especially sex and fertility hormones such as human chorionic gonadotrophin (hCG), estrone-3-glucuronide (E3G), progesterone-3-glucuronide (P3G), luteinising hormone (LH) and follicle stimulating hormone (FSH); and disease markers and diagnostic indicators (e.g. antibodies). Alternatively, the analyte of interest may be particulate e.g. bacterium, virus, yeast, fungus.

A particular advantage of the present invention is that it allows for assays to be conducted using samples which may be turbid, which samples can not be assayed using conventional colourimetric techniques. Examples of samples which are, or may be, turbid include: serum; whole blood; food and drink samples (e.g. milk); samples containing turbid growths of micro-organisms, and the like.

For the purposes of the present specification, the "electroactive portion" of the chemical moiety is defined as that portion which can donate and/or accept an electrical charge when the chemical moiety undergoes a redox reaction. Typically, the electrochemical property which is modulated in the assay will typically be one or more redox potentials. The electroactive portion may comprise one or more groups capable of undergoing oxidation or reduction under the assay conditions, the redox potential of any one or more of such groups being modulated by binding of the binding partner to the electroactive portion. Conveniently the one or more altered redox potentials may be detected by potentiometric or amperometric methods, known to those skilled in the art. Preferably amperometric detection methods (such as chronoamperometry) are employed, as these generate results which are generally easier to measure than potentiometric methods.

Preferably, the modulation of the electrochemical property of the electroactive portion is detected and/or measured by determining the amount of charge transferred to or from the electrically conducting solid support at a particular potential difference. The charge may be transferred between the electroactive portion and the electrically conducting solid support by movement of electrons, and/or ions, and/or other charged particles.

Conveniently, the electroactive portion of the chemical moiety, and the binding partner, are members of a specific binding pair. Advantageously the binding partner comprises an immunoglobulin or an effective portion thereof retaining specific binding activity for the chemical moiety. Effective portions of immunoglobulins therefore include, for example Fv, scFv, Fab, $Fab_2$, and heavy chain variable regions (Hcv, such as those available from llamas and camels) or a chimeric molecule comprising any one or more of the aforementioned portions. Conveniently, the binding partner may be prepared by means of monoclonal antibody techniques or by selection and isolation from an appropriate library of nucleic acid sequences encoding binding partners (e.g. phage display libraries), which are both well known to those skilled in the art.

The electroactive portion of the chemical moiety is conveniently an intrinsic immunogen, or is at least capable of acting as an immunogen (i.e. is a hapten) when conjugated to appropriate carrier molecules (such as bovine serum albumin, or plant peptide derivative etc.). This facilitates the production of immunoglobulins (or effective portions thereof) having specific binding activity for the chemical moiety, which immunoglobulins may act as binding partners in the method of the invention.

In general, the chemical moiety will typically comprise as an electroactive portion an organic, moderately hydrophobic molecule. Examples include organometallic compounds (such as cobalticenium, and ferrocene), and heteroaromatic compounds (such as carbazoles, pyrroles, furans and thiophenes). Desirably the electroactive portion will typically comprise one or more groups readily capable of undergoing oxidation and/or reduction (oxidation being thought of as the removal of an electron, and reduction as the addition of an electron).

Oxidation or reduction will normally result in the creation of electrically charged entities, the effects of which may be stabilised by a conjugated system of electron orbitals in the moiety ("delocalised electrons"). Accordingly, it is preferred that, in the conditions of the assay, the chemical moiety comprises a conjugated system of delocalised electrons. Particular examples of such chemical moieties include pyrroles, furans, thiophenes, and analogues and/or multimers thereof (as described, for example, by Diaz et al., 1979 J. Chem. Soc. Chem. Commun. p635; Niziurski-Mann et al., 1993 J. Am. Chem. Soc. 115, 887; and Waltman et al., 1984 J. Phys. Chem. 88, 4343). The non-bonding electrons of the respective Nitrogen, Oxygen and Sulphur atoms contribute to the conjugated system of electron orbitals. A preferred moiety is N-alkyl carbazole or analogues thereof (in monomeric, dimeric or polymeric forms). FIGS. 1A–D show the general structure of pyrrole, furan, thiophene and carbazole monomers, respectively.

In general it will be desired for the chemical moiety to be immobilised upon a solid support (e.g. an assay dipstick, or a capillary fill chamber). Preferably the chemical moiety will be immobilised upon an electrically conducting portion of the solid support, which electrically conducting portion may comprise, for example, a thin strip of gold, platinum or other conducting metal, a metal oxide, carbon/graphite, silicon, or silicate.

The immobilisation of the chemical moiety upon the solid support may be accomplished in several ways. The present inventors have found that one method is to place a solid support in a solution of a suitable chemical moiety precursor, and then to cause in situ formation of the chemical moiety upon the solid support. Typically, such a process may take the form of causing polymerisation of precursor monomers upon the solid support, resulting in the formation of a mesh-like coating of chemical moiety upon the solid support.

Alternatively, and more preferably the chemical moiety may be immobilised upon the solid support by means of an intervening "pendant" chain portion, preferably one which allows for self-assembly as a monolayer on a supporting surface (as described, for example, by Sabatini & Rubinstein, 1987 J. Phys. Chem. 91, 6663–6669; von Velzen et al., 1994 J. Am. Chem. Soc. 116, 3597–3598; Chidsey et al., 1990 J. Am. en. Soc. 112, 4301–4306; and Rubinstein et al., 1988 Nature 332, 426–429). The chain portion may be thought of as forming an integral part of the chemical moiety.

The use of a pendant portion or molecule is preferred as it separates the electroactive portion from the electrically conducting surface of the electrode (whilst preferably, but not necessarily, retaining a degree of electrical conductivity through, for example a system of delocalized electrons). The pendant portion is typically substantially linear. A preferred pendant portion is an alkyl or alkenyl group (typically comprising 3 to 14, preferably 5 to 12, carbon atoms), which may be substituted or unsubstituted.

In a particular embodiment, an alkyl or alkenyl pendant group is attached to the electrode via a sulphydryl or thiol group—other chemical attachments may be equally suitable.

Another advantage of the use of pendant groups or portions is that they tend to fill in "pin holes" (minor irregularities in the surface of the conducting layer of the electrode), which can have a detrimental effect on the reproducibility of results obtained. It may also be preferred to include excess pendant molecules attached to the electrode (i.e. not every pendant group will necessarily be joined to an electroactive portion). The presence of excess pendant groups is throught to improve the stability and rigidity of the monolayer, which optimises the method/device of the invention. In particular embodiments, the inventors have found that a ratio of four pendant portions to three electroactive portions, may provide optimum results. The excess pendant molecule need not be identical to the pendant portion attached to the electroactive portion: thus, excess pendant "spacer" molecules may be deliberately introduced. Such spacer molecules will conveniently be of a similar nature to the pendant portion of the chemical moiety (e.g. alkyl or alkenyl), but will be no longer in chain length, and possibly shorter, than the pendant portion of the chemical moiety, so as to avoid the possibility that the spacer molecules cause steric hindrance when the binding partner attempts to bind to the electroactive portion.

It is highly preferred that the assay method is such that the analyte of interest need not be identical to the electroactive portion of the chemical moiety to which the binding partner binds. In this way, the assay method may be adapted to detect the presence of any analyte of interest, with the binding partner (typically immunoglobulin) specific for the electroactive portion being required simply as the last step of the assay to generate a detectable signal by binding to the electroactive portion. This preferred feature may be obtained, for example, by utilising competition or displacement type methodologies, as will be explained below.

Accordingly, in preferred embodiments, the binding partner is present as a binding entity, which binding entity comprises first and second specific binding activities. The first specific binding activity is for the electroactive portion of the chemical moiety as aforesaid. The second specific binding activity is typically for the analyte of interest, or for a molecule (such as an immunoglobulin) which itself has specific binding activity for the analyte of interest, such that the presence of the analyte of interest tends to displace the binding entity from a solid support. The binding entity may also possess further specific binding activities, but these are not essential to performance of the invention.

Conveniently the binding entity will be a bispecific antibody or "Diabody" or other bispecific immunoglobulin fragment (e.g. double headed scFv, double headed HCV or a chimeric molecule comprising an scFv and/or an HCV fragment). Alternatively, the binding entity may comprise a non-binding component, to which are attached first and second binding partners having respective first and second specific binding activities. These binding partners may comprise conventional immunoglobulin molecules, such as monospecific antibodies, or effective binding portions thereof (e.g. scFv etc.). The non-binding component may be any substance large enough, and with appropriate chemical properties, for the first and second binding partners to be attached thereto. The non-binding component may be, for example, a peptide, a polypeptide, a liposome or, more conveniently, a particle such as a latex bead. Methods of attachment of immunoglobulins to latex beads are well-known to those skilled in the art.

Conveniently, the method step of causing the binding partner to contact the electroactive portion as a result of the presence of the analyte of interest in the sample is effected by the analyte causing displacement or release of the binding partner from a solid support to which the binding partner is releasably immobilised prior to introduction of the sample. The analyte will typically displace the binding partner from, or compete with the binding partner for binding to, binding sites on the solid support by means of which the binding partner is releasably immobilised.

Thus, in particular embodiments, the assay method involves use of a first solid support upon which is immobilised the chemical moiety, and a second solid support (which may be a separate portion of the first solid support, or a discrete component) upon which is immobilised an analogue of the analyte of interest. The analogue is such that the second specific binding activity of the binding entity will bind to the analogue, albeit with lower affinity than for the analyte of interest. Accordingly, prior to performance of the assay, the binding entity is reversibly immobilised upon the second solid support via its second specific binding activity.

In the presence of free analyte of interest, the analyte will compete with the immobilised analogue for binding to the binding entity via the second specific binding activity. Typically, the affinity of the binding entity for the analyte is greater than that for the analogue, such that the binding entity will be displaced from the second solid support if the analyte of interest is present in the sample. The displaced binding entity is then free to react, via its first specific binding activity, with the electroactive portion of the chemical moiety immobilised on the first solid support, thereby modulating an electrochemical property of the electroactive portion in a detectable manner as aforesaid.

Accordingly, in preferred embodiments, there is an affinity difference between the binding affinity of the analogue and the analyte of interest respectively, such that the presence of the analyte, even at low concentration, will tend to displace the binding entity from the analogue. Alternatively there may be no difference in binding affinity, and the binding entity is displaced from the analogue by competition, e.g. because the analyte of interest is present in the sample at a greater effective concentration than the analogue.

The displaced binding entity may be allowed to diffuse from the second solid support to the first solid support, especially where the first and second supports are in close proximity (e.g. 50 μm–5 mm, preferably 50 μm–1 mm). Alternatively, the binding entity may be transported by capillary action along or through a porous medium, or may be transported by a flow of a fluid sample (e.g. a body fluid such as blood or urine and the like), as disclosed in, for example, WO 91/05262. A pump means (e.g. syringe pump or peristaltic pump) may be provided, if appropriate, to pump fluid comprising released binding entity from the second solid support to the first solid support.

Use of analogues of analytes of interest, in a slightly similar manner, is disclosed and taught, for example, in EP 0 324 540, and in PCT/EP95/04518. Those skilled in the art will appreciate that the analyte of interest will typically be a biological molecule, such as a peptide or polypeptide, or a steroid hormone or the like. Conveniently, the analogue of the analyte of interest will be an epitope mimic, i.e. a molecule (typically smaller than the analyte of interest) generally of synthetic origin, such as a short peptide, which behaves in a manner comparable to the binding site of the analyte to which the binding partner binds. Examples of analytes and suitable analogues are disclosed in EP 0 324 540 and PCT/EP95/04518. The embodiment described above is a variant of known displacement/competition type assays, disclosed inter alia in WO 91/05262 and EP 0 383 313.

In a further embodiment the binding entity is such that the second specific binding activity is for an antibody directed against the analyte of interest. The binding entity may comprise, for example, an analogue of the analyte of interest, which analogue is relatively loosely bound by antibody specific for the analyte of interest, which antibody is immobilised on the second solid support. Alternatively the binding entity may comprise an anti-idiotypic antibody specific for the binding site of the immobilised antibody. In any event, the immobilised antibody conveniently (but not essentially) has a greater affinity for the analyte than for the binding entity, such that the presence of the analyte of interest in the test sample will tend to cause the displacement of the binding entity from the second solid support. The displaced binding entity is then free to bind to the first solid support, via its first specific binding activity, as outlined above.

Methods of immobilising antibodies on solid supports are known to those skilled in the art. Useful discussion is provided by G Hermanson, in "Bioconjugate Techniques" (Academic Press, 1996). Typically the immobilised antibody is covalently coupled by an added functional group. Conveniently the antibody for the analyte may be immobilised by attachment to a further antibody-specific antibody immobilised on the solid support. The first solid support will typically comprise an electrode. The second solid support may be any of those routinely used in assays and include, for example, synthetic plastics materials, microtitre assay plates, latex beads, filters, glass or plastics slides, dipsticks etc. Advantageously, the second solid support comprises a wettable surface.

Conveniently the component of the second aspect of the invention is used to perform an assay of the type disclosed in our co-pending European patent application No. 97309409.7, filed on Nov. 21, 1997. The component might take the form of a relatively cheap, disposable or replacable part for use and interaction with other components (e.g. a separate signal detection means, acting as a reader for the assay result). Alternatively, the component may be provided as an integral part of a larger device.

In a third aspect, the invention provides an assay device comprising the component of the second aspect. Conveniently the device further comprises one or more of the following: sample receiving means for accepting a sample under test; a binding partner having specific binding activity for the electroactive portion of the chemical moiety; detection means for detecting a modulation in an electrochemical property of the electroactive portion of the chemical moiety; data processing means for processing data output from the detection means; and data display means for displaying the assay result, preferably in a numerical form.

The assay device will conveniently comprise a capillary-fill reaction chamber as part of the sample receiving means. In a preferred embodiment the chamber is at least partly defined by the first and second solid supports of the preferred method aspect. Capillary-fill devices which may be adapted for use in the present invention are taught, for example, in U.S. Pat. No. 5,141,868.

In a fourth aspect the invention provides a component for use in the device defined above, said component comprising a solid support having releasably immobilised thereon a binding partner having specific binding activity for an electroactive portion of a chemical moiety, the binding partner being displaced from the solid support in the presence of the analyte of interest, and wherein binding of the binding partner to the electroactive portion directly modulates an electrochemical property of the electroactive portion in a detectable manner. As with the component of the second aspect of the invention, the component may be provided as a relatively cheap, disposable or replacable part for use and interaction with other components (e.g. a separate signal detection means, acting as a reader for the assay result), or may be provided as an integral part of a larger device.

In a fifth aspect, the invention provides a chemical moiety, comprising an electroactive portion, having the structure shown in FIG. 13 wherein: $R_1$ and $R_2$ are independently H; OH; $C_1$–$C_{14}$ alkyl, aryl, alkenyl or alkoxy (all optionally substituted); halide; amide; or amine; and further wherein the heteroaromatic ring structure may be optionally substituted at one or more positions with alkyl, aryl, alkenyl, or alkoxy groups (all themselves optionally substituted), acid groups (organic or inorganic), halide, amide or amine.

Advantageously $R_1$ is alkyl, preferably ethyl, propyl or butyl and preferably $R_2$ is $C_1$–$C_{12}$ alkyl, more preferably $C_4$–$C_8$ alkyl, and most preferably $C_6$ alkyl. It is generally preferred that $R_1$ and $R_2$ are not identical. In a preferred embodiment $R_2$ comprises a (preferably terminally positioned) reactive substituent such as a thiol, carboxyl, amide, amine, halide, aldehyde, ketone, epoxide, or succinimide group, or other protein coupling agent (e.g. as mentioned in Hermanson, "Bioconjugate Techniques", Academic Press, 1996) which facilitates coupling of the moiety to other entities (e.g. solid surfaces). In a preferred embodiment, the chemical moiety is 3,3(N-[6-thiol hexyl] carbazole)N-ethyl carbazole.

The chemical moiety of the fifth aspect of the invention may conveniently be immobilised on an electrically conducting solid support, so as to form a component in accordance with the second aspect of the invention.

In a sixth aspect, the invention provides a molecule having binding specificity for the chemical moiety of the fifth aspect defined above. More particularly the molecule preferably has binding specificity for the electroactive heteroaromatic ring portion of the chemical moiety. The molecule will conveniently comprise an immunoglobulin molecule or an effective portion thereof which retains binding specificity for the chemical moiety—such portions include, for example, Fv scFv, Fab, $Fab_2$, HCV, or a chimeric molecule comprising any one or more of the aforementioned portions. In a preferred embodiment the molecule will comprise at least two binding specificities: a first binding specificity for the chemical moiety, as aforementioned; and a second binding specificity for an analyte of interest or for an antibody (or effective antigen-binding portion thereof) directed against an analyte of interest. It will be apparent to the reader that molecules in accordance with the sixth aspect of the invention will conveniently be suitable for use as a binding partner in performing the method of the first aspect and/or may conveniently be releasably immobilised on a solid support so as to provide a component in accordance with the fourth aspect of the invention.

The invention will now be further described by way of illustrative examples and with reference to the accompanying drawings, in which:

FIGS. 1A–1D show the general structure of pyrroles, furans, thiophenes and carbazoles, respectively;

EXAMPLES

Example 1

This example relates to an illustration of how an assay in accordance with the invention may be performed.

Figure 2:
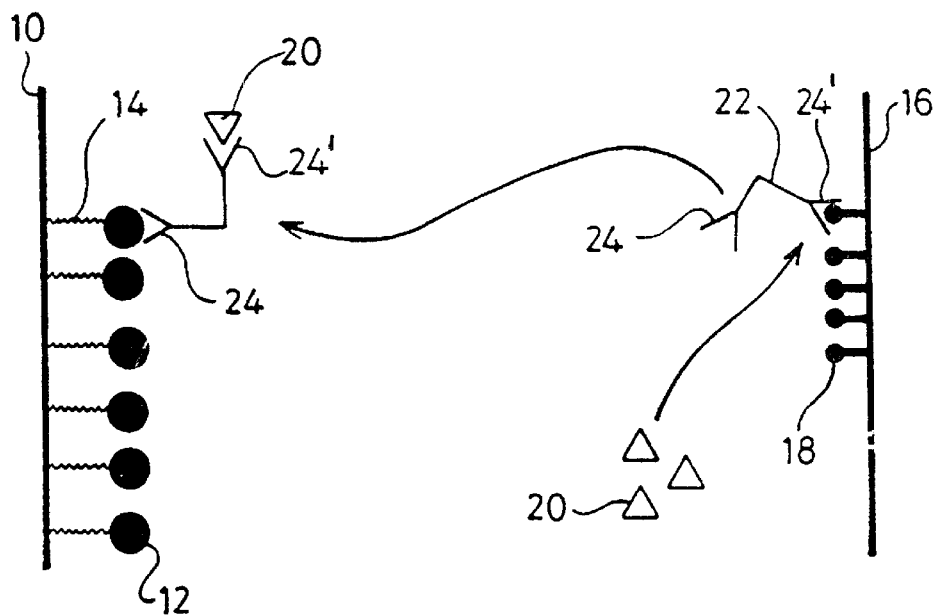
FIGS. 2 and 3 are schematic representations of assays using the method, component and assay device of the invention.

Referring to FIG. 2, there is provided an electrically conducting first solid support 10, upon which is immobilised a chemical moiety 12. The chemical moiety 12 is attached to the first solid support by a "pendant" portion 14, such that a self-assembling monolayer of the chemical moiety 12 is formed on the first solid support 10.

There is also provided a second solid support 16, upon which is immobilised an analogue 18 of the analyte of interest 20. A binding partner 22 is releasably immobilised, via analogue 18, to the second solid support 16. The binding partner 22 is a bispecific antibody, having a first and a second specific binding activity (denoted as 24 and 24' respectively). The first specific binding activity 24 is for the chemical moiety 12. The second specific binding activity 24' is a relatively high binding affinity for the analyte of interest 20, and also confers a relatively low binding affinity for the analogue 18.

Accordingly, upon introduction of a sample comprising the analyte of interest 20, the binding partner 22 is specifically displaced from the second support 16 and is free to bind to the chemical moiety 12 via the second binding activity 24. Binding of the binding partner 22 to the chemical moiety 12 directly modulates a detectable electrochemical property of the chemical moiety 12 (e.g. a redox potential) such that a difference (e.g. in charge, current or potential difference) is detected at the first support 10.

Conveniently first and second solid supports 10, 16 form part of a capillary-fill chamber. into which a test sample is introduced when performing an assay. The physical separation between the binding partner 22 displaced from the second solid support 16 will readily be transported, in a passive manner by diffusion, to the first support 10.

Example 2

Figure 3:
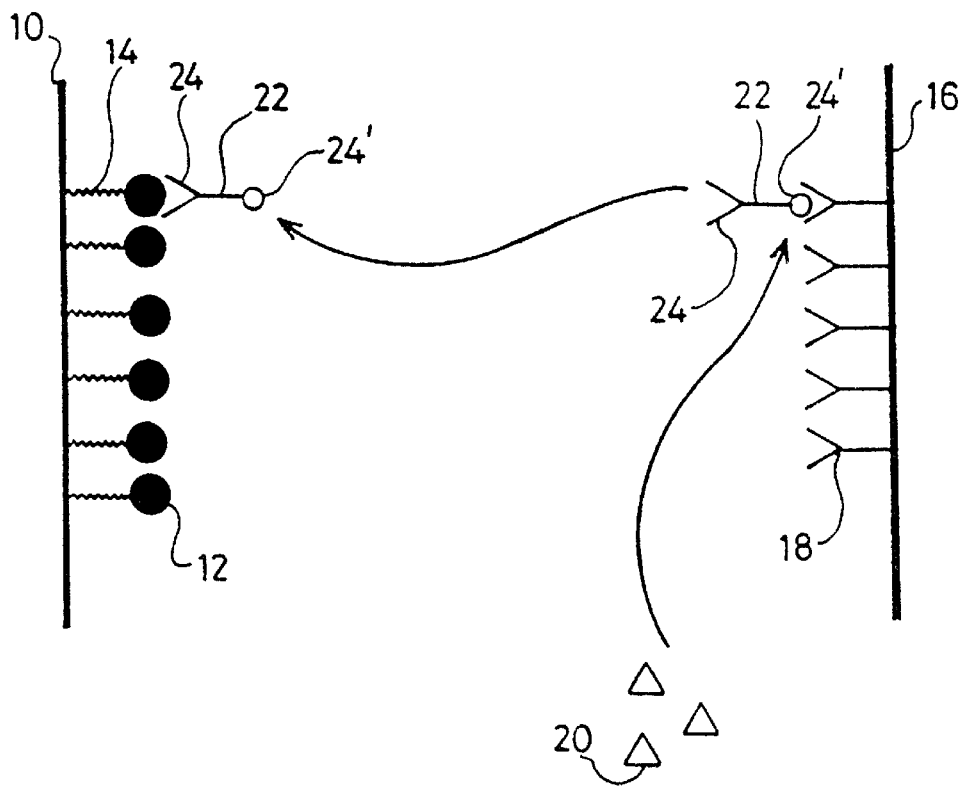

A different embodiment of the method of the invention is illustrated in FIG. 3. Functionally comparable integers are denoted in FIG. 3 by the same reference numerals used in FIG. 2. As with Example 1, the arrangement is conveniently configured for use in a capillary-fill assay device.

In the embodiment illustrated in FIG. 3, the chemical moiety 12 is immobilised on a first solid support 10 as described above. The second solid support 16 is coated with a plurality of molecules of a monoclonal antibody 18 specific for the analyte of interest 20.

The binding partner 22 is a fusion protein comprising an antibody molecule portion 24, and a mimotope portion 24'. The mimotope portion 24' is a peptide "mimic" of the epitope recognised by monoclonal antibody 18 (hence "mimotope"). However, the binding affinity of the antibody 18 is considerably higher (e.g. 10 to 100 times) for the analyte 20 than for the mimotope 24'. Accordingly, the presence of the analyte of interest displaces the binding partner 22 from the solid support 16. The assay then proceeds as described for the embodiment illustrated in FIG. 2.

In some respects, the embodiment shown in FIG. 3 may be preferred, as the binding partner 22 is not bound to the analyte 20 when it binds to the chemical moiety 12—this may be preferable as the presence of the analyte 20 may effect the manner in which the binding partner 22 modulates the electrochemical property of the chemical moiety 12.

Those skilled in the art will appreciate that, using a single chemical moiety 12, the assay method of the invention may be modified so as to be used in the detection of any analyte of interest: one can vary the mimotope portion 24' (in FIG. 3) or the second binding activity 24' (in FIG. 2), such that displacement occurs in response to the presence of the relevant analyte, whilst the first binding activity 24 of the binding partner 22 can remain the same.

Those skilled in the art will also appreciate that Examples 1 and 2 could also be performed as "competition" type assays, in which the concentration of free analyte of interest is sufficient to cause displacement of the binding partner from the second solid support, even though the binding partner may not have a greater binding affinity for the analyte of interest than for the analogue 18 (in Example 1) or antibody 18 (in Example 2).

Example 3

Production of Anti-Carbazole Monomer Antibodies and Electrochemical Characterization Thereof on a Polymeric Carbazole Electrode Surface in Organic Solvent This example relates to the preparation of an electrode, coated with a carbazole electroactive chemical moiety by means of electroplating, which electrode is stable in organic solvents (e.g. dichloromethane). Unless otherwise stated, all reagents are commercially obtainable, and were purchased from Aldrich, USA.

3.1 Synthesis of N-(6-Hexanoic Acid)Carbazole

Carbazole (3.34 g, 20 mmol) was added with sodium hydroxide (4.8 g) to a mixture of water (20 ml) and toluene (20 ml). Cetyltrimethylammonium bromide (1.46 g, 14 mmol) was added as a surfactant to combine the two phases. To this 6-bromo-hexanoic acid was added (5.9 g, 3 mmol) and the solution was left to reflux for 48 hours. The resulting solution was washed with diethyl-ether (3×50 ml) to remove the organic phase. The solvent was then removed via rotary evaporation.

The product was subjected to chromatography over silica gel (acidified) with diethyl-ether petrol (6:4) and the eluate collected in 2 ml aliquots which were checked for presence of product by TLC and detected by UV fluorescence. IR: 3500–2500 (broad) OH (acid), 3000, 2800 (sharp) tertiary amine, 1750 C=O (acid), 1500 tertiary amine. $^1$H NMR: (CDCL$_3$) 10.10 (H, m, OH), 8.06 (2H, m, ArH), 7.62 (6H, t, J 6.35, ArH), 4.05 (2H, t, J 8.82, CH$_2$) 2.15 (2H, m, CH$_2$), 1.75 (2H, m, CH$_2$), 1.56(4H, m, CH$_2$) m/z 281.2 (m$^-$) 180.1 N-methyl carbazole cation.

The acid group in the compound facilitates coupling to carrier molecules, such as bovine serum albumen (BSA) and plant protein derivative (PPD) for various purposes.

3.2 Preparation of Immunogen by Attachment of N-(6-Hexanoic Acid)Carbazole to PPD In order to prepare anti-carbazole antibodies (useful as binding partners to modulate the electrochemical properties of the carbazole), it was necessary to couple the N-(6-hexanoic acid)carbazole to a larger carrier molecule, as the carbazole compound is too small by itself to elicit an antibody response. PPD was selected as the carrier molecule.

The reaction mixture for coupling PPD (plant peptide derivative) was prepared by dissolving 1-ethyl-3-(3-dimethylaminopropyl)carbodimide (40 mg) in MES buffer [2-(N-morpholine)ethane sulfonic acid (aqueous saline pack)](1 ml). Half of this solution (500 μl) was taken and was dissolved in DMF (500 μl). To this N-(6-hexanoic acid)carbazole in DMF (100 mg/ml, 20 mg) was added. This mixture was stirred and watched carefully for any signs of precipitation occurring. If precipitation did appear a small amount of DMF was added to the solution to redissolve the precipitate. To this reaction solution PPD (500 μl) was added slowly and stirred for 24 hours in the dark. The reaction mixture after this time was dialysed for 24 hours against phosphate buffered saline. A fluorimeter scan was taken for the this N-(6-hexanoic acid)carbazole PPD and also for PPD alone on a Perkin Elmer model 5050 fluorimeter (200–400 nm). Peaks were noted for PPD: 200 nm and 390 nm, and for PPD carbazole: 200, 270, 292, 329, 335, 345, 350 and 390 nm. This demonstrated that carbazole was effectively coupled to the carrier molecule.

3.3 Production of Antibodies to Carbazole

Polyclonal antibodies against carbazole were made in a rabbit. A preimmunisation bleed sample was taken to establish background immunity. The rabbit was injected with carbazole/PPD sample (1 mg/ml), with Freund's complete adjuvant at four sites (250 ml each site) and after one week a post immunisation bleed was taken. After one month a second immunisation was made with Freund's incomplete adjuvant with the carbazole/PPD sample (again at four sites). A second post immunisation bleed was one week later. A third bleed was taken one month after the second bleed (with no additional immunisation). Immunisation sites were either side of the spine, two at the front, two at the back. Bleeds were taken from the marginal ear vein. Blood was allowed to clot and serum tested for antibody activity by ELISA, using plates coated with BSA-conjugated carbazole, as described below. Use of the BSA conjugate facilitated coating of the plates with the hapten, whilst the use of a different carrier molecule to that used in the production of antibodies (PPD) ensured that any antibody detected in the ELISA was due to an anti-hapten response rather than an anti-carrier response.

3.4 Synthesis of BSA N-(6-Hexanoic)Carbazole

The N-(6-hexanoic acid)carbazole (50 μl of 100 μg/ml in DMF) was added to N-methyl-morpholine (10 μl). To this isobutyl chloroformate (10 μl) was added and cooled over ice for 5 minutes. The mixture was then transferred (47 μl) to a solution of BSA (2 μl, taken from a stock solution of 6.7 mg of BSA in 500 μl of water and 100 μl of DMF) and stirred for four hours. The sample was transferred to a dialysis tube and dialysed for 48 hours against PBS, changing the PBS solution once. This gave a ratio of 150:1 N-(6-hexanoic acid)carbazole to BSA. Fluorimeter scan: BSA 285 nm, BSA carbazole 285, 329, 335,345, 352, 380, demonstrating effective coupling had taken place.

3.5 ELISA Using BSA N(6-Hexanoic)Carbazole Coated Plates

Microtitre plates were sensitised with the BSA N(6-hexanoic)carbazole (10 mg/ml) made up in sodium carbonate buffer (0.1M, pH 9.6) in PBST (phosphate saline buffer 0.15% tween 20 (Sigma), 200 ml to each well) and incubated at 37° C. for one hour. The plates were then emptied and washed three times with PBST. The plates were then blocked with a 1% solution (in PBST) of skimmed milk powder [Marvel™] 200 ml to each well, and incubated (37° C. for one hour). After this time the plates were emptied and washed in PBST three times as before. The serum was then added at a range of dilutions to the plates (150 ml). This was again left to incubate (37° C. for one hour). The plates were then washed in PBST as before and a ⅟1000 dilution of goat anti-rabbit alkaline phosphatase as conjugate (Zymed Laboratories Inc.) in PBST was added to each well (150 ml). This was left at 37° C. for one hour and the plates washed in PBST as before.

The enzyme substrate was a solution of paranitrophenol phosphate (Sigma Diagnostics) (one tablet) was made up in a buffer solution (5 ml) (diethylamine, pH 9.8, magnesium chloride 50:1). This substrate solution (150 ml) was added to each assay well and the colour was allowed to develop over one hour at room temperature. The results were read on a Dynatech model MR7000 plate reader W/L MODE :dual, Test filter: 405 nm, Ref. filter 570 nm. The results indicated (data omitted for brevity) that a significant anti-hapten response followed boosting, and that anti-hapten antibody levels reached background (control) levels only at dilutions of ⅟3,200 or higher.

3.6 Synthesis of Hexakis[6-(2)-(3)-(Carbazol-9-yl)Hexyl]β-Cyclodextrin

In order to cast electrodes, by electroplating of gold or platinum surfaces in organic solvents, the above carbazole-containing compound was prepared. β-cyclodextrin was readily available in the laboratory, and it was believed that its inclusion would facilitate the formation of a mesh-like coating of the carbazole-containing compound on the electrode.

Sodium hydride (0.15 g, 80% 5 mmol) was weighed out and added to N,N-dimethyl formamide (DMF) (5 ml). β-cyclodextrin (0.567 g, 0.5 mmol) was added slowly to this DMF solution whilst stirring, and left to dissolve completely for 10 minutes. 9-(6-bromohexyl)carbazole (1.25 g, 4 mmol) was added to the mixture and stirred at room temperature for 48 hours.

To the crude product mixture diethyl-ether (200 ml) was added and shaken, leaving an immiscible layer. The organic layer was then removed and water added. This was then left to stir for 90 minutes and allowed to settle for a further 30 minutes. The product was then filtered off, near to dryness, and left in a dessicator at reduced pressure until completely dry (0.78 g, 59.2%). $^1$H NMR 400 mhz (DMSO): 8.10 (2H, m, position 4 and 5, ArH), 7.36 (4H, m, position 2,3,6,7, ArH), 7.10 (2H, m, position 1 and 8, ArH), 5.8–5.7 (secondary alcohol in the unsubstituted β-cyclodextrin), 4.81 (anomeric proton 1H, OCHO, position 1 β-cyclodextrin), 4.5 (primary alcohols in the unsubstituted β-cyclodextrin), 4.36 (2H, m, N—$CH_2$), 4.16 (2H, m, R—O—$CH_2$—$CH_2$), 3.61–3.28 (5H, m, aliphatic protons from the β-cyclodextrin), 1.61 (2H, m, $CH_2$(pendant)) 1.32 (6H, m, 3$CH_2$(pendant)) m/z (FAB$^+$) (The ions corresponding to the hexa-substituted derivative were the most intense in the mass spectrum) 1407 (carb-hexyl)βCD+Na, 1656 (carb-hexyl)$_2$βCD+Na, 1906 (carb-hexyl)$_3$βCD+Na, 2158 (carb-hexyl)$_4$βCD+Na, No peak for (carb-hexyl)$_5$βCD+Na, 2628 (carb-hexyl)$_6$βCD, 2676 (carb-hexyl)$_6$βCD+2Na(M$^+$) 2664 2×(carb-hexyl)$_6$βCD+3Na$^{2+}$.

3.7 Synthesis of Hexakis[6-(2)-(3)-(Carbazol-9-yl)Butyl]β-Cyclodextrin

For comparison, a similar compound to that described in 3.6 above was prepared, but using a butyl pendant portion rather than a hexyl pendant portion. The method of preparation was essentially identical to that described above.

3.8 General Cyclic Voltammetry for Electroplating in Organic Solvents—Experimental Details Cyclic voltammetry was performed on a Princeton Applied Research Corporation Scanning Potentiostat (model 362) together with a Bryans flat bed X-Y recorder (model A25000) and on a EG&G model 273A Princeton Applied Research Potentiostat/Galvanostat. (Using Echem and Lotus 1 2 3 to process the data).

The electrochemical cell consisted of a 25 ml round bottomed flask using a silver wire as a pseudo or quasi-reference electrode, and an aluminium rod as the counter electrode. The working electrode consisted of a clean gold or platinum wire. The electrolyte solution comprised a 0.1 molar solution of tetrabutylammonium hexafluorophosphate in dry dichloromethane (dried over calcium chloride). The carbazole β-cyclodextrin monomer (0.01 g) was dissolved in the electrolyte solution (10 ml). The three electrodes were then placed into the polymer solution and one or two cyclic voltaminetric scans (from 0 volts to 1.5 volts, and then back to 0 volts, at 150 mV per second) were recorded in order to create a polymer film on the working electrode. The electrodes were then transferred to a clean flask with clean electrolyte solution (0.1 molar solution of tetrabutylammoniuim hexafluorophosphate in dry dichloromethane) (10 ml) and about seven scans made or until polymer film showed a stable scan. The polymer was then stably formed on the gold or platinum wire and the electrode could be used for analysis.

3.9 ELA Electrode Assays

The ELISAs performed previously involved binding of antibody to carbazole presented on microtitre plates as a monomer, whereas on the electroplated electrodes the carbazole is present as a dimer. Therefore, in order to determine if the same antibody would still bind to the dimeric carbazole present on the electrodes. EIA electrode assays were performed.

Electrodes were cast in dichloromethane by performance of cyclic voltammetry, as described above. These electrodes were allowed to dry for ten minutes and dipped into anti-carbazole serum at varying dilutions of serum in PBST, (250 μl) and incubated for one hour at 37° C. After this time the electrodes were washed in PBST three times and dried on a tissue. The electrodes were then dipped into goat anti-rabbit alkaline phosphatase conjugate (1/1000, 250 μl) and incubated for one hour (37° C.). The electrodes after this time were washed in PBST as before and then dipped into the para nitrophenolphosphate substrate solution (250 μl) as described for the ELISA and the colour read after one hour.

The results (data omitted for brevity) clearly indicated that a significant amount of the anti-carbazole antibody bound to the electrode, compared to control serum from the pre-immunisation bleed.

3.10 Electrochemical Studies of the Effect of Anticarbazole Antibody by Cyclic Voltammetry and Chronoamperometry Electrodes were cast in dichloromethane as described above (3.8). A final cyclic voltammogram was made and recorded. These electrodes were air dried for ten minutes. The rabbit anti-carbazole serum was diluted to various concentrations, and an electrode was added to each solution (250 μl) for ten minutes. The electrodes were removed and washed in PBST and dried with a tissue. A second cyclic voltammogram was undertaken which was compared to the original and differences could clearly be noted. Sample results are shown in FIGS. 4A (pre-bleed) and 4B (immune serum, containing anti-carbazole antibody).

Figure 4A:
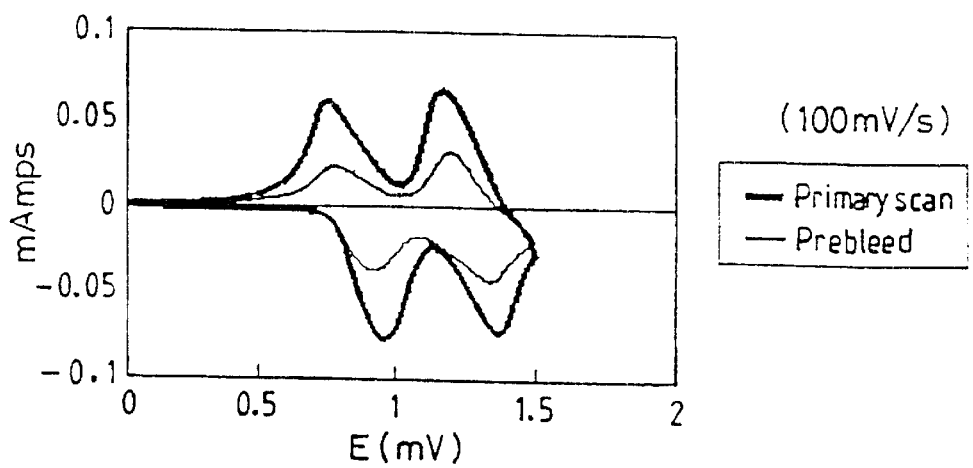
FIGS. 4A and 4B show the results of cyclic voltammograms.
Figure 4B:
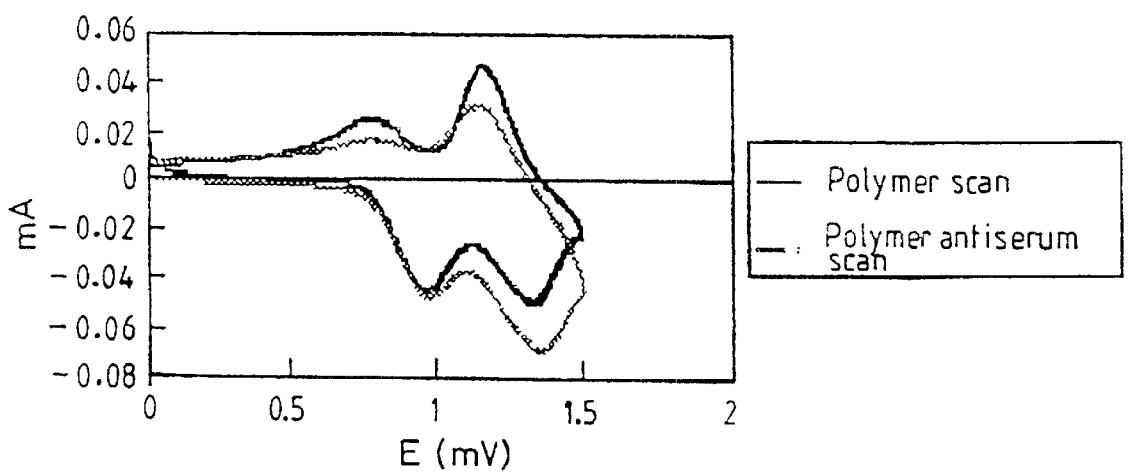

FIG. 4A shows a graph of mA against mV. The thick plot is the trace obtained in the absence of serum, the thin plot is the trace obtained when pre-immunisation serum was added. It can be clearly seen that the pesence of serum markedly dereases the peak heights. FIG. 4B is a similar graph showing the results obtained for polymer alone (in the absence of serum, thick plot) and in the presence of immune serum containing anti-carbazole antibody (thin plot). The effect of the anti-carbazole antibody was to increase the heights of both oxidative peaks (one to a much greater extent than the other), indicated by a greater minus value (i.e. loss of electrons from the carbazole). (Similar experiments were performed using the shorter (butyl) pendant portion carbazole-containing moiety: results were less clear cut, suggesting that the butyl pendant portion is sub-optimal, probably because it is too short to facilitate binding of antibody to the carbazole moiety).

So as to minimise any non-specific effects of serum proteins other than antibody, the antibody fraction was separated from serum by using a protein A affinity chromatography column (PROSEP A, protein A immobilised on glass beads, obtained from Porton products), using conventional techniques. The IgG fraction was eluted off by treating the column with 0.1M citrate (pH 3.4) and collected in 0.5 ml aliquots. These were then neutralised with dilute sodium hydroxide. Elution samples were evaluated by on line UV scanner (360 nM). Total IgG concentration was measured using a Perkin-Elmer Lambda 16 UVDM scanner from 240 to 350 nM. Measurements were taken at 280 nM and the peak absorption placed into Beer's law (A=$\epsilon$cl) where the absorption coefficient of the constant region of IgG ($\epsilon$) is 0.51.

The cyclic voltammetry experiments were then repeated using the protein A treated, IgG-enriched material. Substantially similar results were obtained.

Cyclic voltammetry demonstrated that binding of carbazole-specific IgG to the electrode increased the oxidative peak height, but that such binding also lowered the redox potentials of the carbazole moiety. It was decided that an amperometric measurement method would be more appropriate, and easier to use, than a potentiometric method such as cyclic voltammetry. Accordingly, further analysis was performed by chronoamperometry (i.e. application of a fixed voltage for a period of time). This method can be used to generate a graph of current (I) against time (seconds or milliseconds), and the area under the curve gives a total coulombic charge. This is particularly useful, as an electron has a known colombic charge ($1.602 \times 10^{-19}$), thus one can determine the total number of electrons transferred between the carbazole and the electrode during the experiment.

Figure 5:
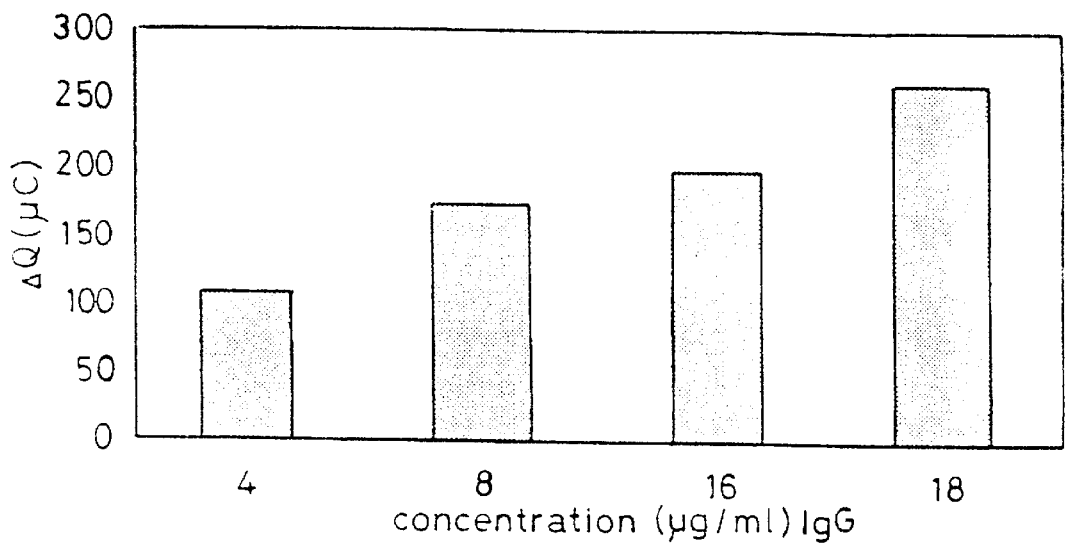
FIG. 5 is a bar chart of ΔQ for different concentrations of IgG.
Figure 8:
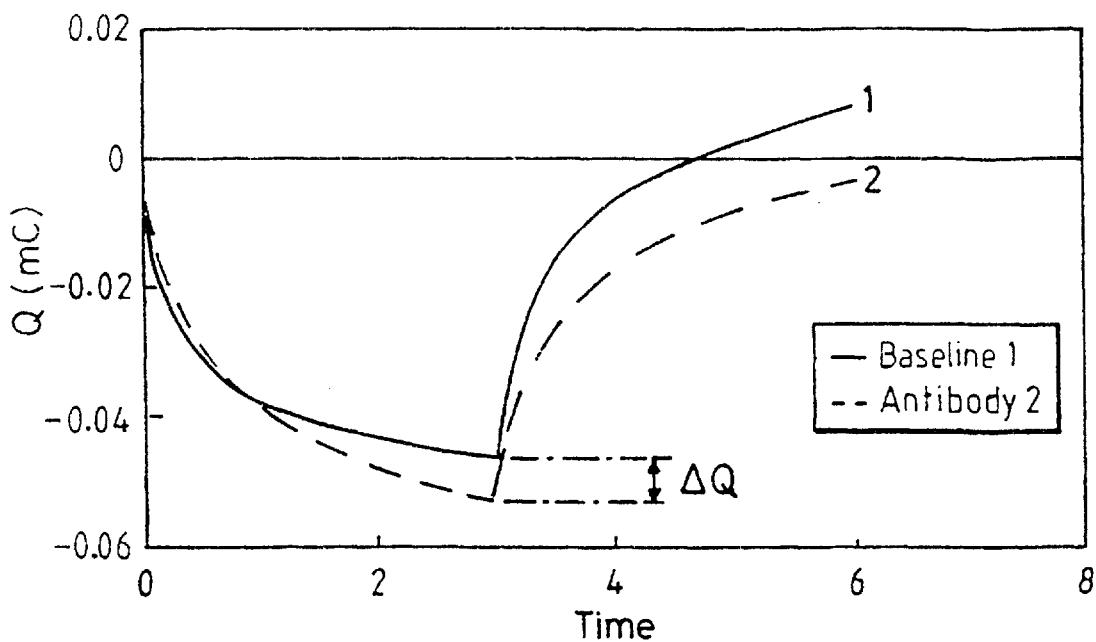

From plots of coulombic charge against time (e.g. as shown in FIG. 8), the difference $\Delta Q$ between the baseline scan and an experimental scan could be calculated. FIG. 5 is a bar chart showing increase in total oxidative electron flow (as measured by $\Delta Q$, in units of $\mu C$) for different concentrations of IgG ($\mu g/ml$) prepared from immune serum. No change in electron flow was observed using control pre-immuisation serum.

Example 4

Electrochemical Characterization of Rabbit Polyclonal Anti-Carbazole Monomer Antibodies on a Carbazole Dimer Monolayer Electrode Surface in Aqueous Conditions Desirably an electrode for use in detecting the presence of an analyte of interest should be stable in water or an aqueous environment, as the majority of samples are, in practice, likely to be aqueous. The inventors found that the electrodes described in the preceding example were not particularly stable in water. It was therefore decided to prepare an alternative electrode in which the electroactive moiety was covalently coupled to the conducting surface, rather than being formed by electroplating and "cast" in situ. In addition, so as to present a more uniform and ordered surface (facilitating antibody binding), it was decided to use a compound which was capable of forming a self-assembling monolayer.

4.1 Formation of N-(6-Bromo Hexyl)Carbazole

Figure 6:
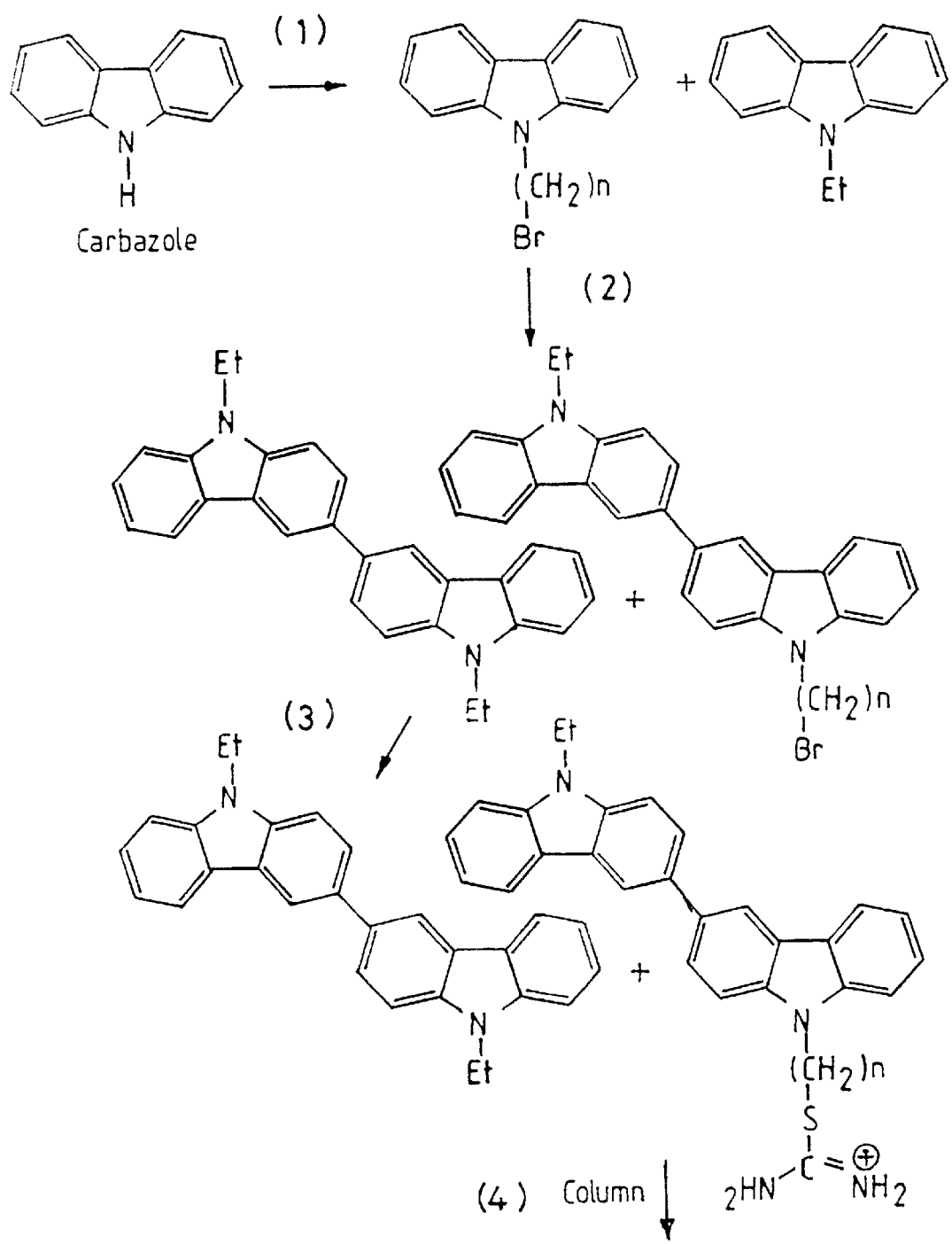
FIG. 6 is a schematic representation of the reaction scheme used to prepare a compound suitable for use in performing the method of, and making a component in accordance with, the present invention.

A mixture of carbazole (1.67 g, 10 mmol), sodium hydroxide (5 g), water (5 mls), toluene (10 mls) and cetyltrimethyl ammonium bromide (0.7 g, 2 mmol) was stirred at room temperature. To this 1-6 dibromohexane (2.3 ml, 30 mmol) was added dropwise (FIG. 6, step 1). This was stirred and refluxed at 170° C. for four hours.

The mixture was allowed to cool and was cleaned, firstly by adding dichloromethane (50 mls) and then by washing with water (3×100 mls). The organic layer was then removed and dried over anhydrous sodium sulphate. The organic layer was then filtered and dichloromethane removed by rotary evaporation. The crude sample was separated over silica gel (diethyl ether/hexane 2:8) and the second spot taken and reduced under vacuum (yield 1.09 gm, 33%). The identity of the compound was confirmed by mass spectrometry (329 M+ion; 249 loss of Br; 180 N-methyl carbazole ion, 167 carbazole; 152 loss of nitrogen from carbazole; 69,55 $C_5H_9$ and $C_4H_7$ ions respectively, from alkyl chain).

4.2 Formation of 3,3(N-[6-Bromo Hexyl]Carbazole)N-ethyl Carbazole)

Electroplating of electrodes was believed to create a surface which contained both monomeric and dimeric carbazole entities. In order to remove any uncertainty, it was desired that a dimeric carbazole entity was prepared at the outset in this example.

Accordingly, N-[bromo hexyl]carbazole (1 g, 3 mmol) from step 4.1 was taken and dissolved in glacial acetic acid (Acros) (75 mls) and perciloric acid (Acros) (70% ww 8 mls). Whilst stirring, ground N-ethyl carbazole (0.8 g, 4 mmol) was added which was followed by 2,3-dichloro-5, 6dicyano-p-benzoquinone (3 g, 13 mmol) (FIG. 6, step 2). The mixture was stirred for one hour after which time a green precipitate of the dimer carbazole was obtained and filtered. The mother liquor was returned to the flask and left overnight. The sample was filtered once again and the combined filtrates were dissolved in acetone (200 ml). A saturated solution of aqueous sodium dithionite (Aldrich) (500 ml) was added to the mixture, which was stirred overnight. The solution changed from a dark green colour to a brown cream colour.

The reaction mixture was then washed with dichloromethane (4×100 mls) to remove the product. The organic layer was then washed with a small amount of water (4×25 mls). The organic layer was then dried over anhydrous sodium sulphate and the solvent removed by rotary evaporation (crude mixture 1.5 gms, yield 83.3%). The identity of the compound was confirmed by mass spectrometry (522 M+ion; 422 loss of HBr; 388 N-ethyl dimer; 329 N(6-bromohexyl)carbazole ion; 179 N-methyl carbazole ion; 129 loss of benzene ring from carbazole; 97 $C_6H_{11}N$, 83 $C_6H_{11}$, and 69 $C_5H_9$, ions respectively).

4.3 Formation of 3,3(N-[6-Thiol Hexyl]Carbazole)N-Ethyl Carbazole

This step involves the addition of a thiol group to facilitate covalent coupling to the gold surface of the electrode.

The crude sample (1.5 g) from 4.2 above was disolved in ethanol 95% (25 ml) and DMF (25 ml) to which thiourea (Aldrich) (0.25 g, 3.3 mmol) was added (FIG. 6, step 3). This was refluxed (6 hours) and then cooled and stirred overnight. The DMF and ethanol was removed by rotary evaporation.

Thin layer chromatography (TLC) of the crude product on silica gel suggested purification could be achieved by first removing the impurities with dichloromethane and eluting the product off the column with DMF (FIG. 6, step 4). Once the product was obtained the DMF was removed by rotary evaporation.

The sample was dissolved in DMF (25 ml) and refluxed. Whilst refluxing sodium hydroxide (0.3 g in 15 ml) was added dropwise (FIG. 6, step 5). This was then left to reflux (4 hours) and allowed to cool. The reaction solution was filtered to remove any precipitation. The sample was then cooled over ice and distilled water (400 ml) added to the solution [some of this material was separated and concentrated by rotary evaporation, to yield the 3,3(N-[6-sodium mercaptan hexyl]carbazole)N-ethyl carbazole salt, which was used to prepare conjugates, as described in 4.5 below].

To precipitate the 3,3(N-[6-thiol hexyl]carbazole)N-ethyl carbazole product concentrated sulphuric acid (10 ml) was added dropwise (FIG. 6, step 6). The product was then filtered through a 5 mm filter and placed in a desiccator (dried indicator silica gel as desiccant) and left under vacuum for three days. (0.22 gms, 94%, pure 4%).

FIG. 6 is a schematic representation of the reaction scheme used to prepare 3,3(N-[6-thiol hexyl]carbazole)N-ethyl carbazole. Step 1 shows the reaction with dibromo hexane, step 2 shows the reaction of N-[bromo hexyl] carbazole with glacial acetic acid, perchloric acid and 2,3-dichloro-5,6dicyano-p-benzoquinone. Step 3 shows the reaction with thiourea. Step 4 represents the TLC purification of the desired salt: 3,3(N-[isothiouronium hexyl] carbazole)N-ethyl carbazole, and steps 5 and 6 represent the reactions with sodium hydroxide and sulphuric acid respectively.

4.4 Formation of 3,3(N-[6-Thiol Undecyl]Carbazole)N-Ethyl Carbazole

An essentially identical compound to that above was prepared, except that the compound comprised a longer (unedcyl, $C_{11}$) pendant portion. The synthetic technique was essentially identical as described in 4.2 and 4.3, except that 1-11dibromo-undecane (0.7 g, 15 mmol) was used in place of dibromo hexane.

4.5 Formation of Conjugates Comprising Hexyl Carbazole Dimers

Conjugates of the dimeric carbazole compounds were prepared for the purposes of production and ELISA testing of antibodies, since the polyclonal antiserum prepared previously (3.3) was raised against monomeric carbazole and would not necessarily recognise the compounds in dimeric form. Accordingly, the carbazole dimers were used to prepare conjugates with keyhole limpet haemocyanin (KLH) for immunisation, and to prepare conjugates with bovine serum albumen (BSA), as described below.

(i) Formation of KLH (Keyhole Limpet Haemocyanin) Carbazole Conjugate

Maleimide-activated KLH (Pierce 2 mg) was dissolved in PBS (phosphate buffered saline) (200 µl). To this, 3,3(N-[6-sodium mercaptan hexyl]carbazole)N-ethyl cabazole (2 mg in 200 µl of PBS) was added and the mixture stirred at room temperature in a ReactiVial™ (Pierce). The sample was then dialysed in a Slide-A-Lyzer (Pierce) dialysis cassette in PBS for 2 hours. The PBS was then changed and the sample left to dialyse overnight at room temperature. The sample was then removed and made up to 2.5 ml with PBS and placed onto a PD10 column (Pierce) and removed off the column in a 3.5 ml aliquot of PBS. The sample volume was reduced by spin filtration. UV scans taken showed that 50 to 60 carbazole dimers were bound to the carrier protein, indicating that half the available sites were filled. The KLH conjugate was used for immunisation, essentially as described in 3.3.

(ii) Formation of BSA Carbazole Conjugate

BSA (Pierce, 8 mg) was dissolved in PBS (1 ml) and to this solution was added SPDP (N-succinimidyl-3-[2-pyridyldithio]propionate) (2.1 mg) in DMSO (25 µl) and incubated, stirred at room temperature (1 hour). The mixture was taken and made up to 2.5 ml in PBS and loaded onto a PD10 column. The sample was then removed from the column with 3.5 ml of PBS. The sample was placed into a ReactiVial™ to which 3,3(N-[6-sodium mercaptan hexyl] carbazole)N-ethyl cabazole (4 mg in 200 ml of PBS) was added and stirred at room temperature overnight. The sample was then dialysed in a Slide-A-Lyzer (Pierce) dialysis cassette in PBS for 2 hours. The PBS was then changed and the sample left to dialyse overnight at room temperature. The sample was then removed and made up to 2.5 ml and placed onto a PD10 column (Pierce) and removed from the column in a 3.5 ml aliquot. UV scans taken showed that 5 to 8 carbazole dimers were bound to the carrier protein, indicating that half the available sites were filled. (Essentially similar techniques were used to prepare ovalbumen [OVA] conjugates, starting from maleimide activated OVA (Pierce, 2 mgs), and OVA conjugates were occasionally used in place of BSA conjugates).

The BSA conjugates were used to coat ELISA plates, essentially as described previously. ELISAs performed using BSA conjugate-coated Greiner microtitre plates demonstrated that the antibody raised against the KLH conjugate successfully bound to the dimeric carbazole molecules (data omitted for brevity).

4.6 Formation of 3,3(N-(6-thiolhexyl)carbazole)N-ethyl Carbazole Monolayer on a Gold Surface A gold electrode surface was cleaned by polishing. Monolayers were formed by immersing a polished screen printed planar electrode (3 mm by 7 mm) into a solution of the 3,3(N-(6-thiol hexyl)carbazole)N-ethyl carbazole (approximately 0.01M in DMF). This was left for 24 hours at room temperature in the dark. The electrodes were removed and washed in dichloromethane and then placed into clean dichloromethane to soak overnight in the dark at room temperature.

In some experiments, the monolayer also comprised spacer pendant molecules (without electroactive portions), formed by dipping the electrode in a mixture of the 3,3(N-(6-thiol hexyl)carbazole)N-ethyl carbazole solution together with a thiol alkane (typically a $C_4$ molecule).

4.7 Electrochemistry of 3,3(N-(6-thiol hexyl)carbazole)N-ethyl Carbazole Monolayer Electrochemistry was performed using an EG&G model 273A Princeton Applied Research Potentiostat/Galvanostat and using Echem and Lotus 123 to process the data so obtained.

(i) Electrochemistry in Organic Solvent

The dichloromethane electrochemistry was performed with a cell comprising a silver wire as a pseudo or quasi-reference electrode, an aluminium rod as the counter electrode and the monolayer on the gold surface as the working electrode. The electrolyte solution comprised of a 0.1 molar solution of tetrabutylanmonium hexafluorophosphate in dry dichloromethane. The electrode was removed from the stock solution and rinsed in dichloromethane. The electrode was then placed in dried dichloromethane and left to soak overnight in the dark at room temperature.

The electrode was dried in a stream of nitrogen. To check the electrochemistry of the monolayer, the electrode was transferred to a cell containing dried dichloromethane with tetrabutylammonium hexafluorophosphate (0.1M) as the electrolyte. The cell contained a silver pseudo reference electrode and an aluminium rod as the counter electrode. Cyclic voltammograms (100 mV/sec 0 to 1.1 to 0 V) were repeated until a stable, reproducible scan could be achieved. The cyclic voltammograms of the monolayer were found to be different to the electroplated carbazole polymer cyclic voltammograms. The pure dimeric monolayer produced a single redox peak process, rather than the two peak voltammogram observed with the cast electrodes (described in Example 3).

(ii) Electrochemistry in Aqueous Conditions

Working electrodes were transferred through stages of acetonitrile:water mixes before being placed in the aqueous solution (for conducting electrochemical analysis in aqueous environments), as follows: the electrode was left to soak for 15 minutes in acetonitrile. After this time the electrode was removed and 8 mls of the solution was taken and 2 mls of the solution was discarded. The solution was made up to 10 mls with MilliQ water and the electrode returned to the acetonitrile:water mix to soak for 15 minutes. The process of discarding 2 mls of the acetonitrile:water mix and making up to 10 mls with MiliQ water was repeated four times, each time being soaked for 15 minutes. The acetonitrile:water mix was then discarded and the electrode rinsed in a stream of water and left for final soak in clean MiliQ water for 15 minutes. This totalled six soaking periods from pure acetonitrile to pure water. This had the effect of improving the cyclic voltammograms obtained by allowing for gradual acclimatization of the electrode to an aqueous environment, and hence formation of a more stable monolayer.

Figure 14:
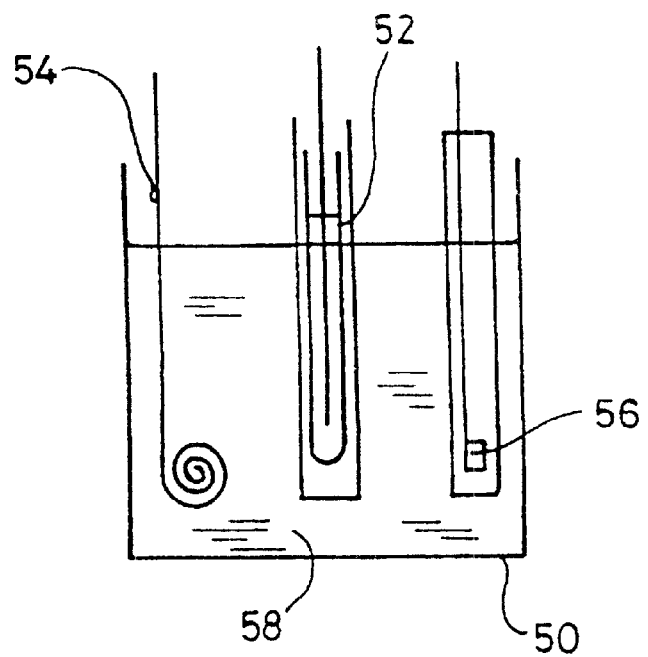
FIG. 14 is a schematic representation of an electrochemical cell used to investigate electrochemical properties of various electrode coatings.

Electrochemistry in an aqueous environment was performed with a cell, the arrangement of which is illustrated schematically in FIG. 14. Referring to FIG. 14, the cell was formed in a 100 ml class beaker (50) and comprised a Sure Flow™ (Orion, UK) Ag/AgCl (inner)—KCl (outer) reference electrode (52), a clean, coiled platinum counter electrode (54) and a gold working electrode with the bound monolayer (56). The electrolyte solution (58) was sodium hexafluorophosphate in deionised water (unles stated otherwise). (The electrical connections of the components are omitted from FIG. 14 for the sake of clarity). The working monolayer electrode was placed into this cell and a cyclic voltammogram taken at 100 mV/sec from 0 to 0.6 V and then to −0.1V and back to 0 V. Repeated scans (about six) were made until a stable cyclic voltammogram was obtained.

As previously, the method of analysis was then changed to chronoamperometry so that any current effects could be observed and measured. Assays were again repeated until a stable, reproducible scan could be formed to provide a base line.

4.8 Using the Monolayer as an Analyte Detector in Aqueous Conditions

An electrode, stabilized in aqueous conditions as described above, was dried with tissue, taking care not to damage the monolayer surface. A test or a control sample (with or without anti-carbazole antibody) was then pipetted onto the electrode surface (25 μl, at 0.14 mgs/ml total Ig) and the electrode left on a flat surface at room temperature for 15 minutes. After this time the electrode was shaken dry and washed in a stream of water. The electrode was then returned to the cell and a chronoamperometric scan taken under the same condition as the baseline scan. To enable comparison two samples were used: one sample (the control) contained no anti-carbazole IgG (pre-immunisation serum sample); the other sample contained the relevant anti-carbazole IgG (the antibody sample). Thus, the pre-immunisation serum sample is a negative control sample, whilst the antibody sample was expected to show an effect from binding of the relevant antibody to the carbazole.

Figure 7:
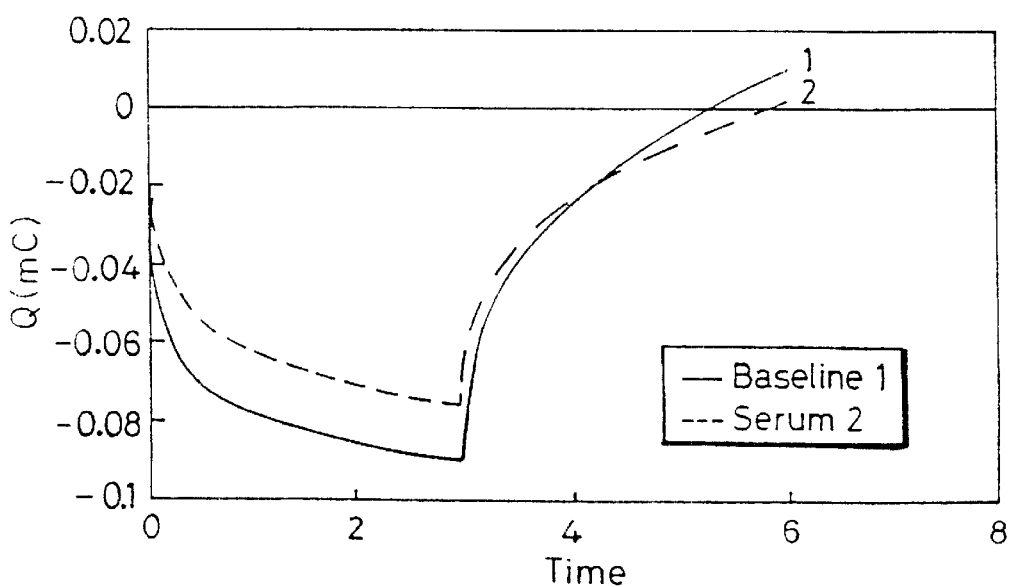
FIGS. 7 to 9 are graphs of mC against time.
Figure 9:
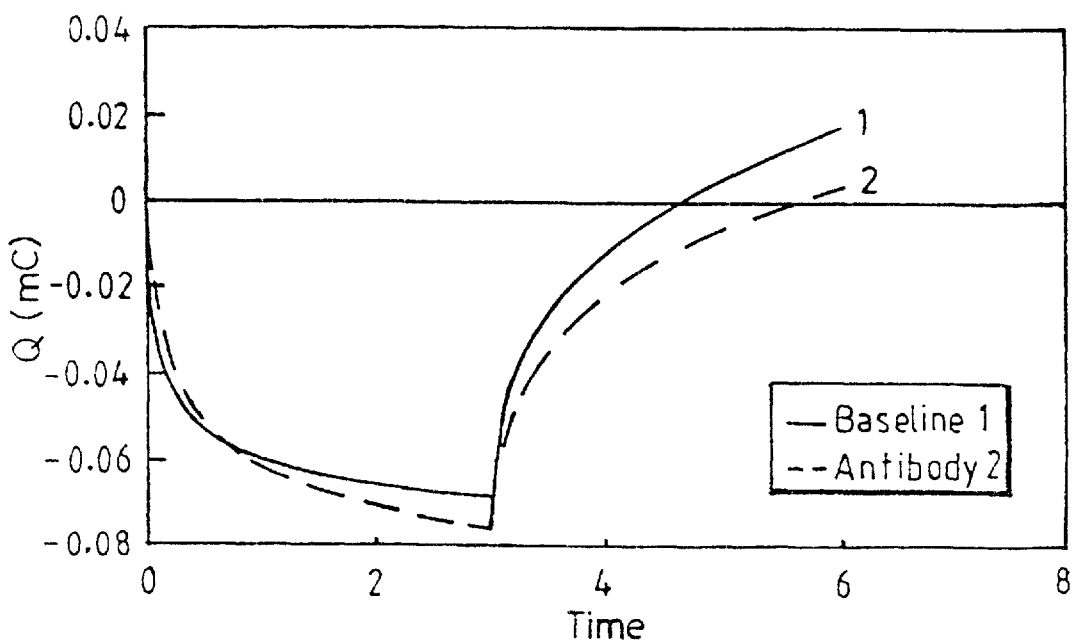

The results show that, as anticipated, the negative control scan gave a reduced peak value, as indicated in FIG. 7. FIG. 7 shows a graph of mC against time. The baseline plot is labelled 1, and the plot obtained in the presence of pre-immune serum is labelled 2. Conversely, duplicate samples of electrodes treated with immune anti-carbazole antibody exhibited scans with a peak height increased by 7.73 mC (FIG. 8) and 7.18 mC (FIG. 9) respectively. Again, in FIGS. 8 and 9, baseline plots are labelled 1, experimental plots in the presence of antibody are labelled 2.

Example 5

Preparation of an Alternative Electrode Surface Production of (Ferrocenylcarbonyloxyl)Undecyl Thiol The above-mentioned material was synthesised for use as an alternative electroactive chemical moiety for attachment to a solid support. Ferrocene carboxylic acid (3.45 g, 15 mmole) was dissolved in heptane (50 ml) and oxyalyl chloride (9.5 g, 75 mmole) and stirred for one hour. The reaction mixture was then heated to dissolve the remaining carboxylic acid and stirred for a further 45 minutes. The solvent was reduced under vacuum to remove the excess oxalyl chloride. Heptane (30 mls×2) was added and reduced under vacuum to make sure all remaining traces of oxalyl chloride are removed. This left the resulting ferrocene carboxylic acid chloride as a dark red compound.

The ferrocene carboxylic acid chloride was dissolved in dichloromethane (150 mls) with 11-bromoundecenanol (3.46 g, 13.8 mmole) and triethylamine (3 g, 30 mmole) and stirred at room temperature for 2 days. The reaction mixture was separated over silica gel using dichloromethane as the solvent. The resulting product was 11-(ferroceneyl carbonyloxyl)undecane bromide.

Sodium hydrosulphate hydrate (Aldrich 1 g×20 mmol) was ground in to a powder and dissolved into DMF (50 ml) and stirred at room temperature. To this 11-(ferroceneyl carbonyloxy)undecane bromide (0.5 g, 10 mmol) was added and refluxed (60° C.) for one hour to yield the (ferrocenylcarbonyloxyl)undecyl thiol.

Additionally, conjugates of the ferrocenylcarbonyl undecane compound were prepared, using KLH and BSA, in order to facilitate the raising and testing of antibodies against the electroactive hapten. KLH conjugates were prepared essentially as described previously for the carbazole compound (4.5(i)), starting from maleimide-activated KLH, except that the KLH was allowed to react with (ferrocenylcarbonyloxyl)undecyl thiol (2 mg in 50 μl DMSO/150 μl PBS), instead of the carbazole compound. Similarly, BSA conjugates were prepared exactly as described in (4.5(ii)), but using the ferrocenyl compound instead of the carbazole compound.

The KLH conjugate was used to raise anti-(ferocenylcarbonyloxyl)undecyl antibodies in rabbits, as described above for the production of anti-carbazole antibodies (3.3), and tested by ELISA on BSA conjugate-coated microtitre plates, as described previously (3.5). The results (omitted for brevity) showed that a good hapten-specific response was obtained, and that polyclonal sera from boosted rabbits gave above-background anti-hapten ELISA responses at serum dilutions in excess of 1/1,000.

Example 6

Having demonstrated that binding of anti-carbazole antibodies to the monolayer of carbazole dimers could be successfully detected directly by electrochemical assay, the inventors set out to devise an assay for an analyte of interest, Estrone-3-glucuronide (E3G), based on this principle. The first step in the formulation of such an assay was the preparation of a bispecific anti-E3G/anti-carbazole antibody construct.

6.1 Isolation of the scFv4155 Anti-E3G Antibody Fragment

The DNA encoding the scFv with a specificity towards E3G was isolated from the hybridoma cell line 4155 and was assembled in an *E. coli* expression plasmid pHEN, essentially as described by Ward et al. (Nature 1989 341, 544). The active corresponding antibody fragment was isolated via phage display as a fusion protein with the gene III protein of modified M13. The scFv was tagged at the C-terminus of the VL with a peptide sequence containing polyhistidine residues for purification purposes and a sequence recognised by a second antibody (anti hydrophil II) for detection. (The antibody anti hydrohil II is disclosed, and a method of obtaining it taught, in EP 0 456 790, wherein the antibody is referred to as "anti hydrophilic tail"). The DNA sequence of the resulting construct is shown as Seq. ID. NO: 1 in the attached sequence listing. The amino acid sequence of the encoded polypeptide is shown as Seq. ID. NO: 2 in the attached sequence listing.

6.2 Isolation of the Anti-carbazole HCV Fragments HCV3 and HCV24

The genes encoding the anti carbazole HC-V domains were isolated essentially as described below. The genes were cloned into an M13 phage display plasmid as a gene III fusion using the restriction endonucleases Pst I and Bst EII via standard molecular biological procedures. Briefly:

(i) Isolation of Gene Fragments Encoding Ilama HC-V Domains

A llama was immunised eight times at 2–4 week intervals with carbazole coupled to the carrier PPD (250–500 µg conjugate per immunisation). Five days after the last immunisation, a blood sample of about 200 ml was taken and an enriched lymphocyte population was obtained via Ficoll (Pharmacia) discontinuous gradient centrifugation. From these cells, total RNA was isolated by acid guanidium thiocyanate extraction (e.g. via the method described by Chomczynnski and Sacchi, 1987). After first strand cDNA synthesis (using the Amersham first strand cDNA kit), DNA fragments encoding HC-V fragments and part of the long or short hinge region were amplified by PCR using specific primers $V_H$-2B, Lam-07 and Lam-08:

```
                PstI
V_H-2B      5'-AGGTSMARCTGCAGSAGTCWGG-3'   (SEQ. ID. NO: 3)
S = C and G, M = A and C, R = A and G, W = A and T, Lam-07      HindIII
5'-AACAGTTAAGCTTCCGCTTGCGGCCGCGGAGCTGGGGTCTTCGCTGTGGTGCG-3'
(SEQ. ID. NO: 4)

Lam-08      HindIII
5'-AACAGTTAAGCTTCCGCTTGCGGCCGCTGGTTGTGGTTTTGGTGTCTTGGGTT-3'
(SEQ. ID. NO:5).
```

Upon digestion of the PCR fragments with PstI (coinciding with codon 4 and 5 of the HC-V domain, encoding the amino acids L-Q) and BstEII (located at the 3'-end of the HC-V gene fragments, coinciding with the amino acid sequence Q-V-T), the DNA fragments with a length between 300 and 400 bp (encoding the HC-V domain, but lacking the first three and the last three codons) were purified via gel electrophoresis and isolation from the agarose gel. These PstI/BstEII fragments were inserted into a modified pHEN based phage display vector linking the HCV genes to gene III of M13 via a HIS6-myc sequence. This library was transformed into E. coli XL-1 Blue by electroporation yielding 2.7×10⁶ individual transformants.

(ii) Selection of Carbazole Binding HCV Fragments Using Affinity Panning

Phages expressing HCV fragments at the tip were prepared by starting 15 mL 2TY/Amp/Glucose with 50 µL of the anti-carbazole library and was grown until the culture had reached log-phase ($A_{600}$=0.3–0.5). M13K07 helper phage was added and the culture was incubated for 30 minutes at 37° C. without shaking. The infected cells were spun at 5000 rpm for 10 minutes and the cell pellet was resuspended in 200 mL 2×TY/Amp/Kan. After overnight incubation at 37° C. the cells were removed by centrifugation. The phages were isolated from the supernatant by PEG precipitation: add ⅕ volume PEG/NaCL (20% Polyethylene glycol 8000, 2.5M NaCL) mix well and leave in ice-water for 1 hour; pellet the phage particles by centrifugation at 8000 rpm for 30 minutes; resuspend the phage pellet in 20 mL water and add 4 mL PEG/NaCl solution; mix and leave for 15 minutes in ice-water; pellet the phage particles by centrifugation at 5000 rpm for 15 minutes; and resuspend the phage pellet in 2 mL PBS with 2% Marvel.

Nunc-immunotubes (5 mL) coated overnight at 37° C. with 1 mL OVA-carbazole in carbonate buffer (100 mg/ml), were washed 3 times with PBS and blocked with PBS containing 2% Marvel at 37° C. for 1 hour. 1 mL phage suspension was added to the tube (and to a control tube) and incubated for 2 hours at room temperature with occasional shaking. Unbound phages were removed by washing the tube 20 times with PBS-T followed by 20 washes with PBS. Bound phages were eluted using 1 mL elution buffer (0.1M HCL/glycine pH2.2/1 mg/mL BSA). After 15 minutes at room temperature the mixture was neutralised by adding 60 mL 2M Tris. The eluted phage were recovered by adding 9 mL log-phase E. coli XL-1 Blue (in addition 10 µl of the eluted phages was used to infect log phase E. coli D29AI). Also 4 mL log-phase E. coli XL-1 Blue was added to the immunotube. Both cultures were incubated for 30 minutes at 37° C. without shaking to allow infection. The fraction were pooled and serial dilutions of $10^{-1}$ to $10^{-6}$ were plated out on 2TY/Amp/Glucose selective plates.

| Results of selection experiment: | |
| --- | --- |
| phage input per tube: | $10^{13}$ |
| phages recovered from control tube: | $5 \times 10^4$ |
| phages recovered from OVA-carbazole coated plate: | $3 \times 10^6$ |

(iii) Isolation of Specific Carbazole Binding HC-V Domains

For the production of soluble HC-V fragments with a HIS6myc-tail, individual colonies (in E. coli strain D29AI) obtained after one round of panning, were grown in a 96 well microtiter plate containing 200 µl 2TY/Amp/Glucose medium per well. Once the cultures reached $OD_{600}$=0.5, 150 µl of these cultures was tranferred into a V-bottom 96 well plate and the cells were pelleted by centrifugation. The E. coli cell pellets were resuspended in 200 µl 2TY/Amp/IPTG and incubated (with shaking) at 25° C. overnight. The presence of specific carbazole binding HC-V fragments in the supernatants was determined as follows:

Microtiter plates sensitized with OVA, BSA, OVA-carbazole or BSA-carbazole in carbonate buffer (100 µg/ml) were washed once with PBS-T and incubated with 200 µL blocking buffer (1%BSA in PBS-T) per well for 1 hour at 37° C., then: the E. coli supernatants were mixed with equal volumes of blocking buffer; 50 μL of these samples was added to each well of the sensitized microtiter plate, the antibody fragments were allowed to bind to the antigen at 37° C. for 1 hour; unbound HCVs were removed by 4 washes with PBS-T; 100 μL of an 1 μg/mL solution of the monoclonal-anti-myc antibody Nr 4111 (in blocking buffer) was added to each well and incubated at 37° C. for 1 hour; all unbound antibody removed by 4 washes with PBS-T; 100 μL of an appropriate dilution of an alkaline-phosphatase conjugated anti-mouse antibody (in blocking buffer) was added to each well (incubate at 37° C. for 1 hour); all unbound conjugated antibody removed by 4 washes with PBS-T; and alkaline phosphatase activity detected by adding 100 mL substrate solution to each well (1 mg/ml pNPP in 1M diethanolamine/1 mM $MgCl_2$).

In this way a number of specific anti-carbazole HC-V fragments were isolated, among which were two termed HCV3 and HCV24 respectively. The DNA and amino acid sequences of HCV3 are shown as SEQ. ID. NO:s 6 and 7 respectively in the attached sequence listing. The DNA and amino acid sequences of HCV24 are shown as SEQ. ID. NO:s 8 and 9 respectively in the attached sequence listing. The antigen binding specificity of these fragments was determined via ELISA, which showed that the fragments possessed the desired anti-carbazole binding activity.

Ammonium thiocyanate (ATC) sensitivity (a relative measure for binding strength) of the HCV-carbazole interaction was determined to be 0.5M both for HCV3 and HCV24 (value=ATC concentration at which binding signal was 50% of maximal) using the protocol essentially as described above with inclusion of various concentrations of ATC together with the HCV containing supernatants.

6.3 Expression and Purification of Anti-carbazole HCV Domains

Figure 10:
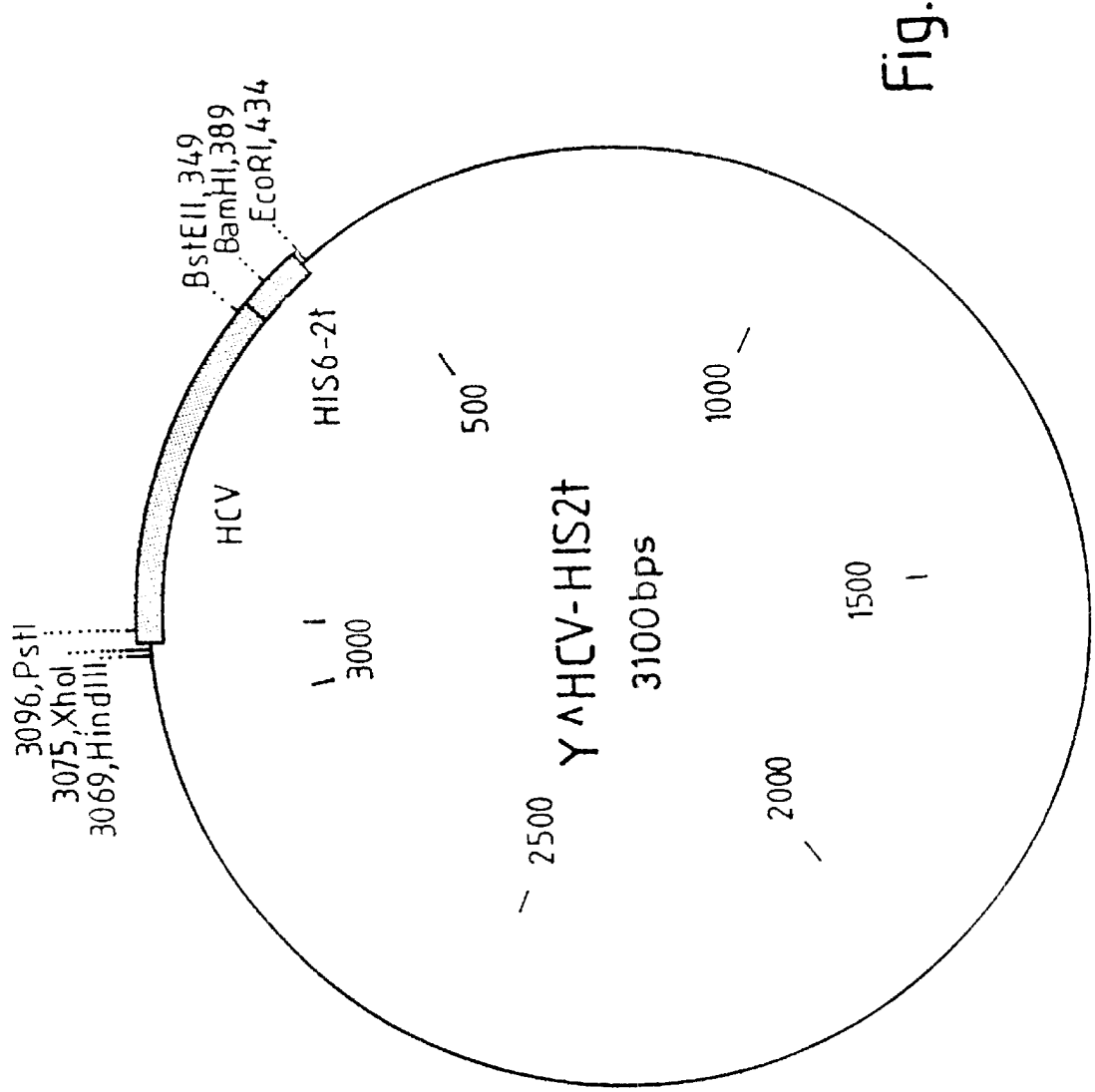
FIGS. 10–12 are schematic representations of plasmid constructs useful for obtaining reagents suitable for use in the method of the present invention.
Figure 11:
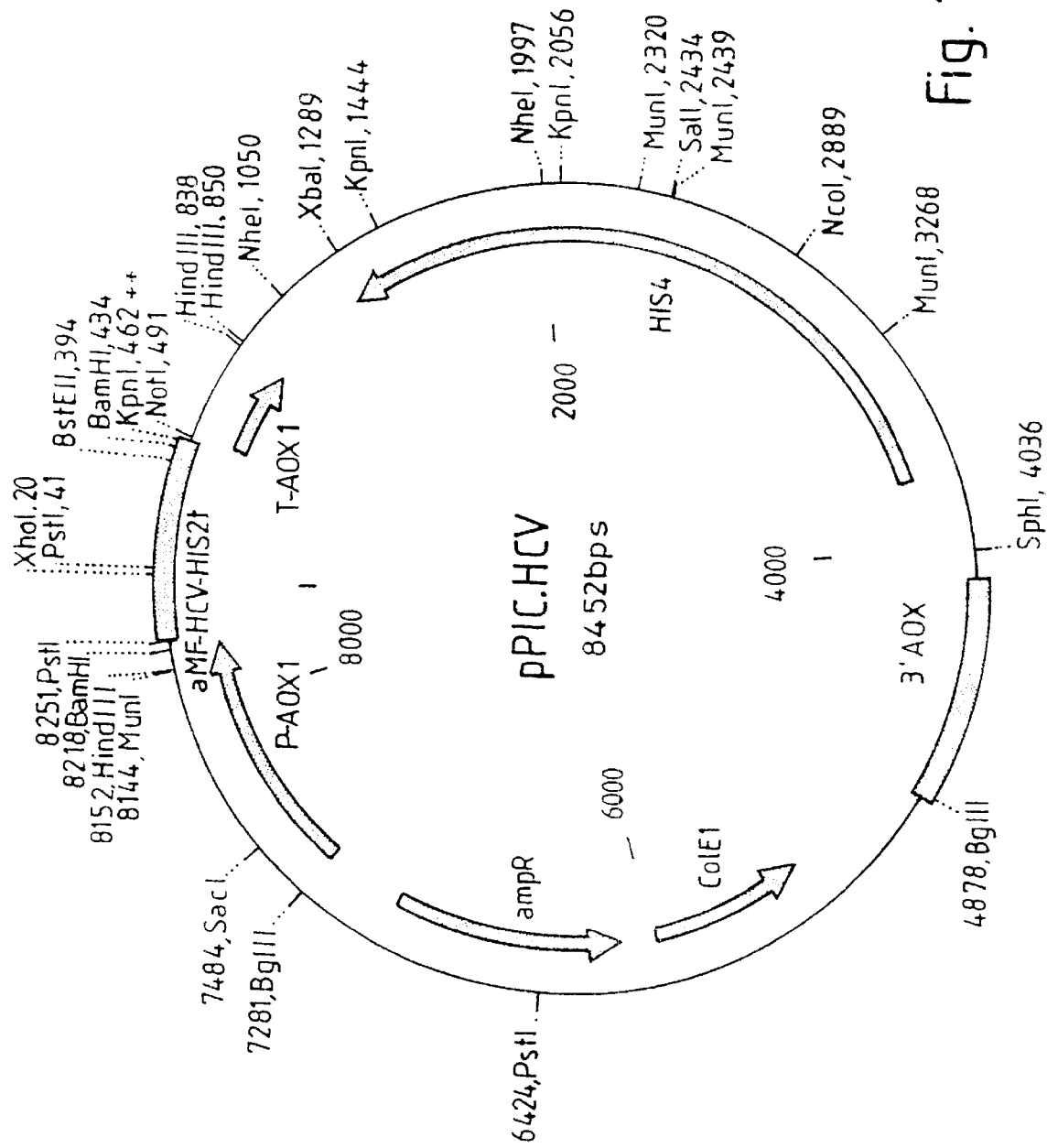

The PstI/BstEII HCV3 and HCV24 gene fragments were subcloned into the *P. pastoris* transformation/expression vector pPIC9. This involved two cloning steps: in the first step the PstI/BstEII HCV3 and HCV24 fragments from the phage display vector pUR4536 were subcloned into the pUC.Y^HIS2t shuttle vector thus yielding pUC.Y^HCV3-HIS2t and pUC.Y^HCV24-HIS2t respectively. FIG. 10 shows a map of plasmid Y^HCV-HIS2t constructs. In a subsequent step the XhoI/EcoRI HCV-HIS2t fragments were excised from these intermediates and inserted into XhoI/EcoRI opened pPIC9 yielding pPIC.HCV3-HIS2t and pPIC.HCV24-HIS2t. FIG. 11 shows a map of plasmid pPIC.HCV constructs. The amino acid sequence of the expression products of pPIC.HCV3-HIS2t and pPIC.HCV24-HIS2t are shown as SEQ.ID. NO.s 10 and 11 in the attached sequence listing.

*P. pastoris* cells were transformed essentially as recommended by the supplier of the *P. pastoris* expression system (Invitrogen). Briefly, *P. pastoris* GS115 cells were grown overnight at 30° C. in 500 ml YPD medium (1% Yeast Extract, 2% Peptone, 1% Glucose) to $OD_{600}$=1.4. The cells were spun and the pellet was washed with sterile distilled water before resuspending in 100 ml KDTT buffer (50 mM Potassium Phosphate pH7.5, 25 mM DTT). After 15 minutes incubation at 37° C. the cells were pelleted (3 minutes, 3000 rpm) and resuspended in 100 ml ice-cold STM buffer (92.4 g Glucose/l, 10 mM Tris.HCL pH7.5, 1 mM $MgCl_2$).

After 5 washes with this buffer the cell pellet was resuspended in a final volume of 0.5 ml STM buffer. Approximately 2–5 μg DNA in 2 μl $H_2O$ (BglII digested pPIC constructs: DNA purified via phenol/chloroform extractions and precipitation) was mixed with 70 μl of fresh competent *P. pastoris* cells (on ice). The cells were electroporated in a 0.2 cm cuvette at 1.5 kV, 400Ω, 25 μF in a BioRad Gene-Pulser. Immediately after electroporation, 1 ml of YPD medium was added to the cells. After recovery for 1 h at 30° C., the cells were pelleted and resuspended in 200 μL 1M Sorbitol and plated out onto MD plates (1.34%YNB, $4×10^{-5}$% Biotin, 1% Glucose, 0.15% Agar). Colonies formed by transformed cells (His$^+$) were visible within 48 hours incubation at 30° C. Transformed *P. pastoris* cells GS115 were selected essentially as recommended by the Invitrogen *Pichia pastoris* expression manual. The plates containing the His$^{31}$ transformants were used to screen for the Mut' and Mut$^s$ phenotype as follows: Using sterile toothpicks, colonies were patched on both an MM plate (1.34%YNB, $4×10^{-5}$% Biotin, 0.5% MeOH, 0.15% Agar) and an MD plate, in a regular pattern, making sure to patch the MM plate first. Approximately 100 transformants were picked for each construct. After incubating the plates at 30° C. for 2–3 days the plates were scored. Colonies that grow normally on the MD plates but show little or no growth on the MM plates were classified as Mut$^s$ clones.

Transformed and selected *P. pastoris* clones were induced to express HCV domains using the protocol outlined below: i) a single colony from the MD plate was used to inoculate 10 ml of BMGY (1% Yeast Extract, 2% Peptone, 100 mM potassium phosphate pH6.0, 1.34%YNB, $4×10^{-5}$% Biotin, 1% Glycerol) in a 50 ml Falcon tube; ii) the culture was grown at 30° C. in a shaking incubator (250 rpm) until the culture reached an $OD_{600}$=2–8; iii) cultures were spun at 2000 g for 5 min. and resuspended cells in 2 ml of BMMY medium (1% Yeast Extract, 2% Peptone, 100 mM potassium phosphate pH6.0, 1.34%YNB, $4×10^{-5}$% Biotin, 0.5% Glycerol); iv) cultures were returned to the incubator; v) 20 μL of MeOH was added to the cultures after 24 h to maintain induction; and vi) after 48 h the supernatant was harvested by removing the cells by centrifugation.

Individual supernatants were assayed by SDS-PAGE and ELISA and single HCV domain producing clones were used to scaled up this process to yield larger amounts of antibody fragment.

Culture supernatants (200 mL, pH 6–8) were clarified through a 0.45μ low protein binding cellulose acetate filter (Nalge Nunc Intl.), applied to a Ni-NTA Superflow column (5 mL, Qiagen Ltd. UK) at 2 mL/min, and washed with PBSA until the absorbance at 280 nm reached baseline. Elution with a linear gradient of 0–500 mM imidazole over 5 column volumes was followed by immediate buffer exchange by passage down a column of G-25 Sepadex (150 mL bed volume, Pharmacia) pre-equilibrated with PBSA, collecting 4 mL fractions. Peak fractions were assayed by SDS-PAGE and ELISA then combined and freeze dried in aliquots.

6.4 Construction of the Bispecific scFv4155-HCV3 and HCV24 Constructs

Figure 12:
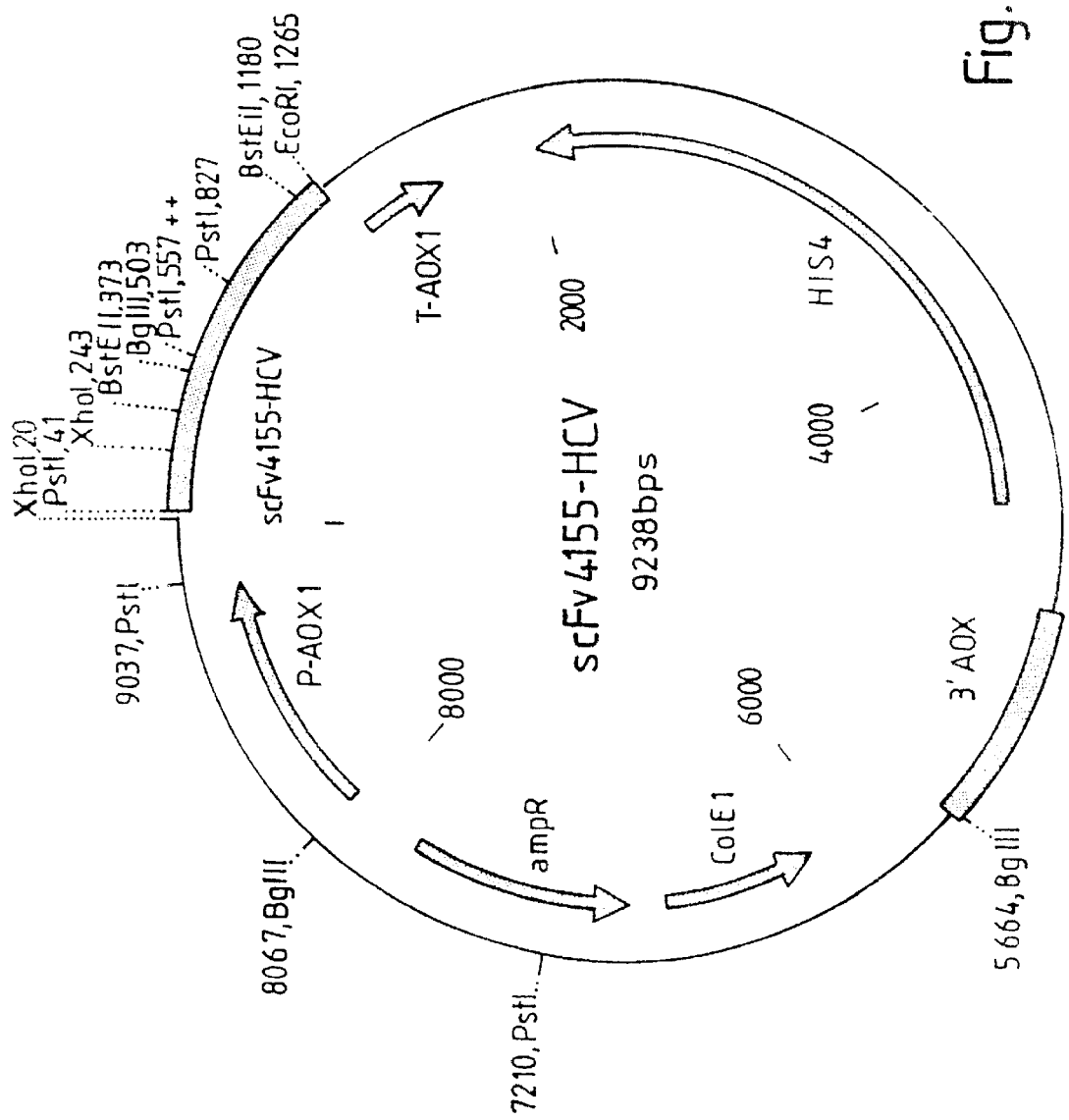
Figure 13:
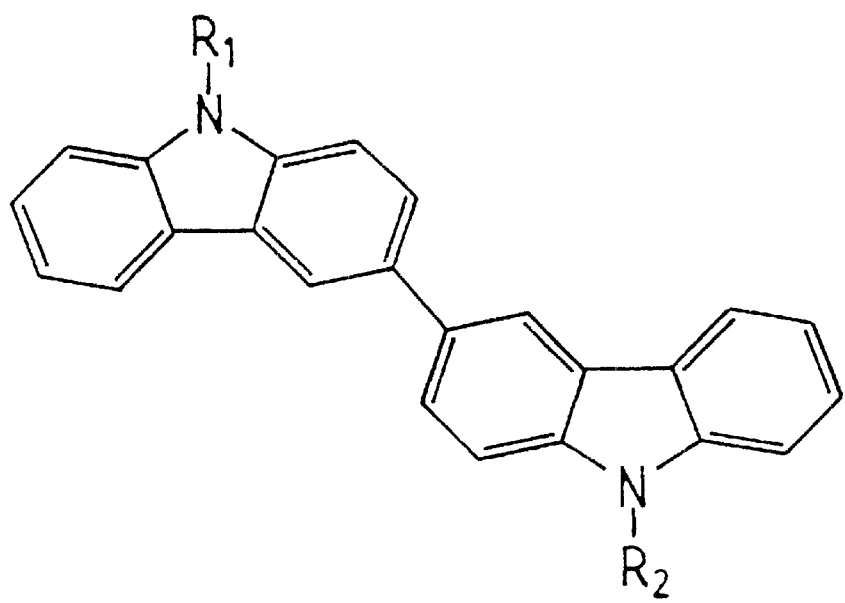
FIG. 13 is a schematic representation of a chemical moiety of use in performing various aspects of the invention.

The construction of the scFv4155-HCV3-HIS2t and scFv4155-HCV24-HIS2t bispecific antibody fragments involved two cloning steps. In the first step a synthetic XhoI/PstI fragment (from pUR4124: a pUC vector containing VL-Lys-synthetic linker-VH-Lys EcoRI/HindIII insert: the DNA and encoded amino acid sequences are shown as SEQ. ID. NO:s 12 and 13 respectively in the attached sequence listing), encoding a flexible polypeptide linker which allows the fusion of the C-terminus of the scFv4155 and the N-terminus of the HCV fragments, was inserted into XhoI/PstI opened Y^HCV3-HIS2t and Y^HCV24-HIS2t thus yielding Y.link-HCV3-HIS2t and Y.link-HCV24-HIS2t respectively. In the second step, the XhoI/EcoRI fragments from the Y.link-HCV-HIS2t constructs were inserted into BstEII/EcoRI opened pIC.scFv4155-HIS2t together with a VL4155 encoding BstEII/XhoI fragment (isolated from the same vector) yielding pPIC.scFv4155-link-HCV3.HIS2t and pPIC.scFv4155-link-HCV24.HIS2t respectively. FIG. 12 shows a map of constructs based on plasmid pPIC.scFv4155-HCV. The amino acid sequence of the expression product of pPIC.scFv4155-link-HCV3. HIS2t and of pPIC.scFv4155-link-HCV24.HIS2t are shown as SEQ. ID. NO:s 14 and 15 respectively in the attached sequence listing.

P. pastoris transformants were isolated essentially as described under 6.3 except that the pPIC DNA was digested with DraI instead of BglII before transformation. The crude P. pastoris supernatants were tested for the production of scFv-HCV fusion protein via analysis on 12% acrylamide gels using the Bio-Rad mini-Protean II system. E3G, carbazole and bispecific binding activity was shown via ELISA as follows: (a) 96 well ELISA plates (Greiner HC plates) were activated overnight at 37° C. with 200 $\mu$l/well of the OVA-E3G or OVA-carbazole conjugate; (b) following one wash with PBST the wells were incubated for 1 hour at 37° C. with 200 $\mu$L blocking buffer per well (Blocking buffer: 1% BSA in PBS-T); (c) serial dilutions of test samples (100 $\mu$L) were mixed with equal volumes of blocking buffer and added to the sensitised ELISA wells. Plates were incubated at 37° C. for 1–2 hours; (d) 100 $\mu$L anti-hydrophil-II monoclonal (Clone Nr 4890) in blocking buffer was added to each well and incubated at 37° C. for 1 hours; (e) unbound antibody was removed by 4 washes with PBS-T; (f) 100 $\mu$L of an appropriate dilution of an alkaline-phosphatase conjugated anti-mouse antibody (in blocking buffer) was added to each well (incubate at 37° C. for 1 hour); and (g) unbound conjugated antibody was removed by 4 washes with PBS-T. Alkaline phosphatase activity was detected by adding 100 mL substrate solution to each well (1 mg/ml pNPP in 1M diethanolamine/1 mM $MgCl_2$).

Alternatively, the presence of bispecific carbazole/E3G binding HC-V fragments was detected by allowing the fragments to bind to an OVA-carbazole coated plate and detecting E3G binding activity by a subsequent incubation with E3G-AP conjugate. Following one wash with PBST, captured E3G-AP was detected by adding 100 $\mu$l/well pNPP substrate (1 mg/mL pNPP in 1M diethanolamine/1 mM $MgCl_2$). In summary, the results showed that the scFv4155-HCV3 and scFv4155-HCV24 bispecific molecules were able to bind to both E3G and to carbazole.

Example 7

Assay for Estrone-3-Glucuronide

Having obtained a bispecific immunoglobulin molecule with the desired two binding specificities, the inventors were able to perform an assay to determine the presence of an E3G analyte of interest in accordance with the invention.

7.1 Construction of Electrochemical Sensing Layer

An electrode was prepared according to the description in Example 4.6.

7.2 Construction of Cell for Electrochemical Measurements (reference numerals refer to the integers shown in FIG. 2)

Strips of thin plastic sheet, approximately 0.5 mm thick, were used as a spacer and stuck to the electrode support surface surrounding the electrode (10 in FIG. 2) using double sided adhesive tape. Thus a chamber 0.5 mm deep was formed surrounding the gold electrode, creating a capillary-fill device. This allowed 50 $\mu$l of sample to be placed over the electrode for incubations. In a second version, a plastic lid was placed over the chamber but leaving the two ends open. Checks showed that 10 $\mu$l of liquid was sufficient to fill the chamber and electrochemical measurements could be performed to provide almost identical results to those obtained with the lid absent.

7.3 Formation of E3G and ED3G Conjugates

An estrone 3-glucuronide (E3G) or estradiol 3-glucuronide (ED3G) ovalbumin conjugate was prepared by resuspending 2.6 mg of E3G or ED3G in 2 ml of freshly prepared solution of EDC (1-ethyl(dimethylaminopropyl) carbodimide, 1.0M) and NHS (N-hydroxysuccinimide, 0.02M) and incubating for 15 mins at room temperature.

To the E3G or ED3G solution, 2 ml of ovalbumin (10 mg/ml) was added and this was incubated for 2.5 hr at room temperature with constant mixing.

The conjugated E3G or ED3G ovalbumin solution was then dialysed for 16 hr against 1 L of phosphate buffered saline containing 0.1% sodium azide.

7.4 Construction of Immunochemical Surface

The surface of the lid (16) facing the electrode, which was typically polycarbonate or polystyrene, was modified to form an assay surface (18). Estrone-3-glucuronide (for competition assay) or estradiol-3-glucuronide (for displacement assay) conjugated to ovalbumin, as in example 7.3 above, was allowed to adsorb to the plastic surface by incubating it with a 0.5 mg/ml solution in phosphate buffered saline pH 7.2 (PBS) for 2 hours at room temperature. The surface was rinsed with PBS to remove excess conjugate and dried using a hot hair drier for thirty seconds. The surface was then loaded with the double headed antibody scFv4155-HCV3 (22), described in Example 6, by incubating the surface with a solution (100 $\mu$g/ml in PBS) of the double head for thirty minutes at room temperature.

7.5 Preparation of Cell for Electrochemical Measurements

A stable base line scan was obtained for a cell, without the lid on, as described in Example 4.7 (ii).

7.6 Assay for Estrone-3-Glucuronide (E3G)

The electrode was dried using a stream of nitrogen. Excess antibody was rinsed off the surface with PBS and the lid (16) shaken free of liquid, or in one experiment air dried without noticable effect on the assay result, before attaching it over the electrode chamber. Immediately, the chamber was filled with the sample to be measured (20). In this example the samples were solutions of E3G made up to known concentrations (0–50 $\mu$g/ml) in PBS. For samples containing E3G, double headed antibody was displaced or competed off from the immunochemical surface thereby allowing it to bind to the carbazole dimer groups (12) on the electrode surface. The cell was established as described in 4.7(ii) and left to react for 20 minutes.

7.7 Measurement of the Electrochemical Response

The capillary was shaken empty and washed with distilled water. The electrolyte solution was then returned to the capillary-fill device and an electrical reading, here chronoamperometric, measured (as in 4.7(ii)), compared to the background scan and the $\Delta Q$ value calculated as described in example 3.10.

7.8 Assay Curve

Figure 15:
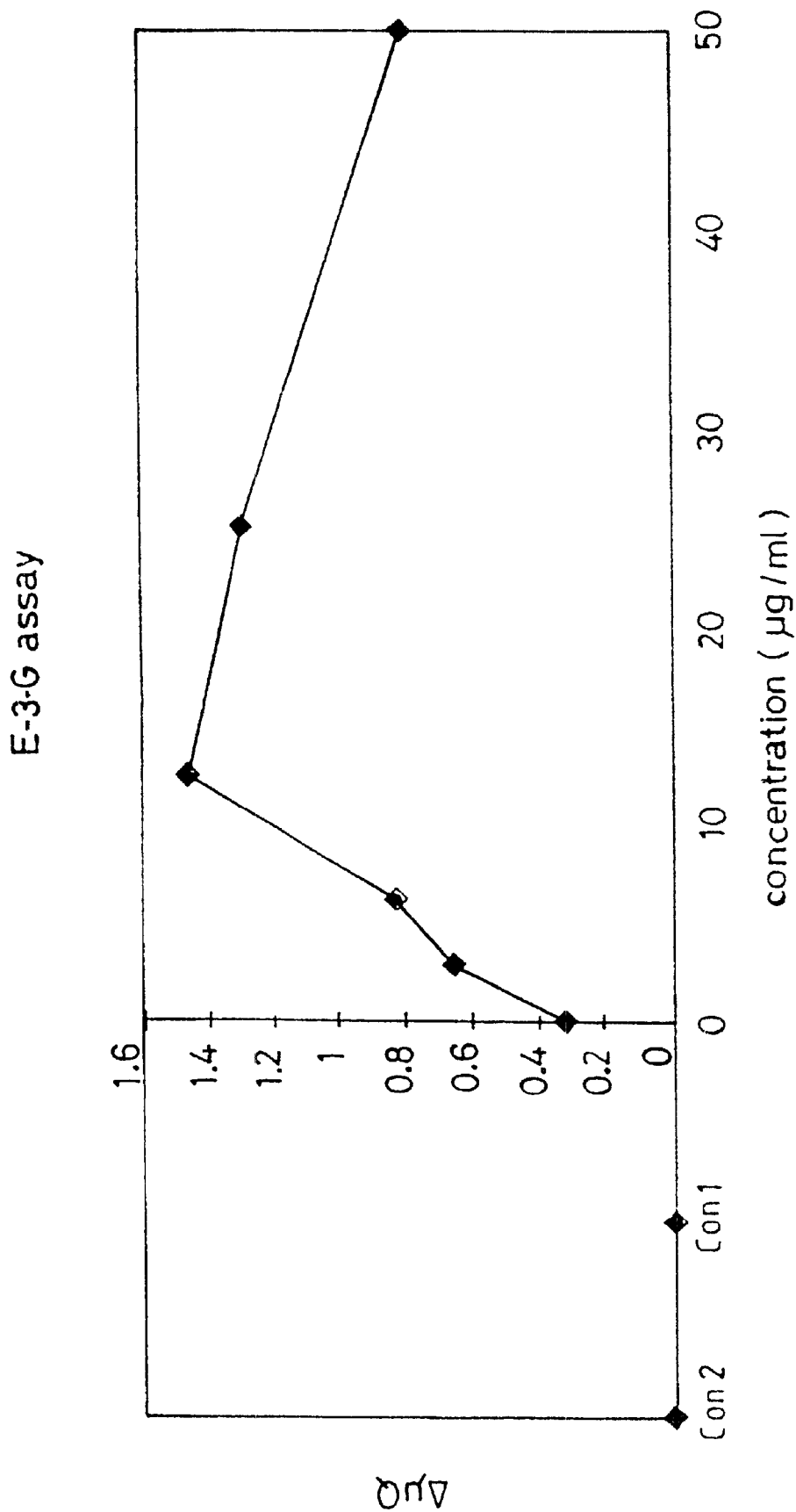
FIG. 15 is a graph showing a dose response curve for an assay device in accordance with the invention used in accordance with the method of the invention to detect the presence of an E3G analyte of interest.

FIG. 15 shows an assay curve (dose response, $\Delta \mu Q$ against concentration of E3G in $\mu$g/ml) for a set of 8 cells challenged with increasing concentrations of the analyte E3G. A typical immunoassay curve shape is seen. A peak response was obtained at a concentration of E3G between 10 and 20 $\mu$g/ml. Two important controls are also illustrated in the Figure: PBS (Con2) or E3G (50 $\mu$g/ml) in PBS (Con1), in the absence of double headed antibody, caused no electrochemical changes.

7.9 Assay with Reduced Chamber Depth

Figure 16:
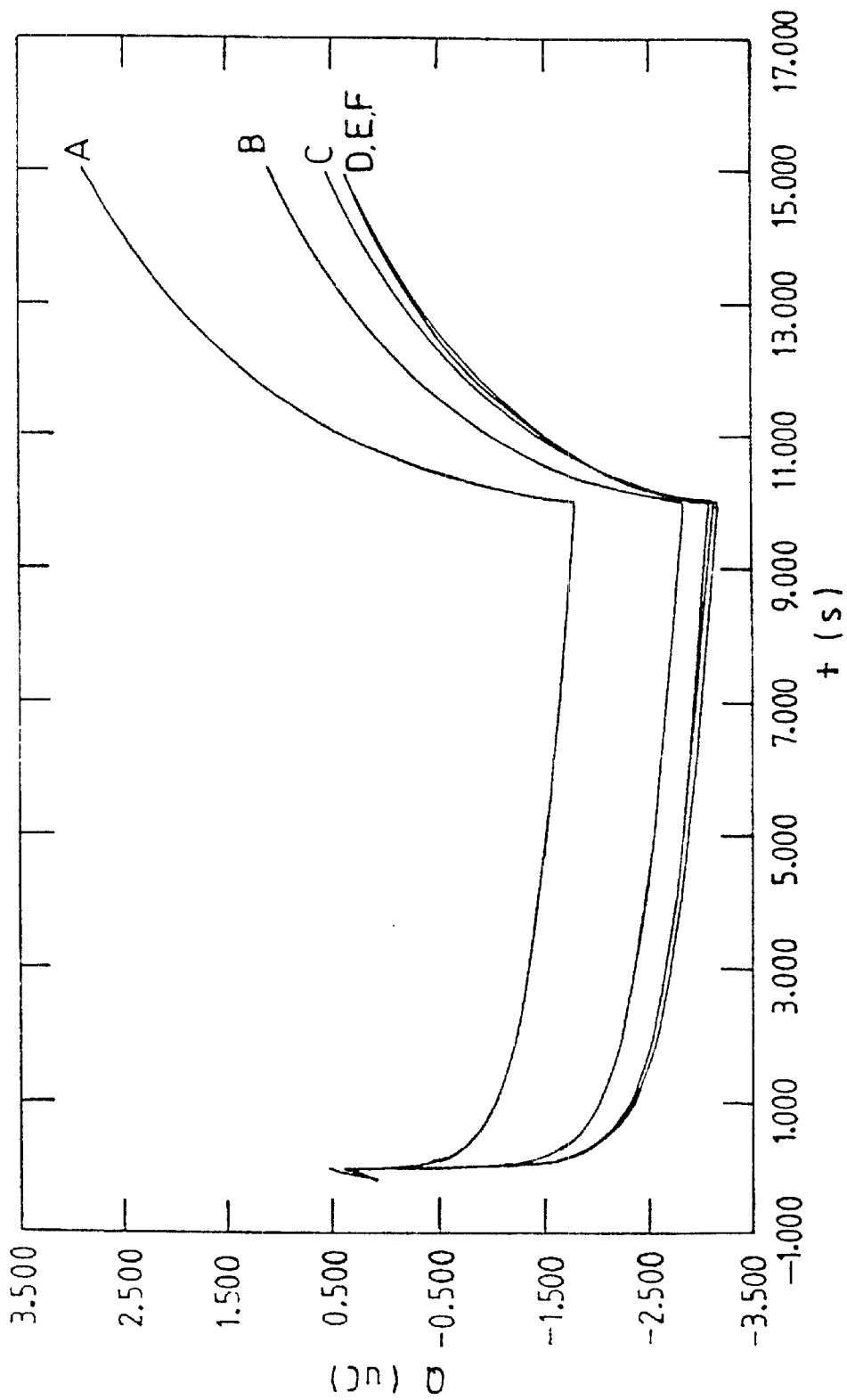
FIG. 16 is a graph of $\mu$C against time.

In a further experiment the chamber depth was reduced by using double-sided adhesive tape alone as a spacer (giving about a five fold reduction in chamber depth, to around 0.1 mm), and the assay repeated substantially as described above. A beaker was filled with E3G sample solution (25 μg/ml), which solution entered the capillary device by capillary action. A scan was performed as soon as possible (after about 20 seconds), and further scans made thereafter at about 1 minute intervals. The results, shown in FIG. 16 (μC against time in seconds) demonstrated very rapid signal development (with a maximum value of ΔQ obtained after just one or two minutes), showing that the device allows for real time monitoring and analysis of samples. Referring to FIG. 16, (A) is the background scan, (B) the scan obtained after 20 seconds, and (C), (D), (E) and (F) the scans obtained after 1, 2, 3 and 4 minutes respectively. It can be seen that there was essentially no further change in the scan profile after 1–2 minutes.

---

What is claimed is:

1. A detection component for use in a device for detection of an analyte in a sample, comprising:
   (a) an electrically conducting solid support;
   (b) a chemical moiety immobilized on the solid support, said chemical moiety comprising an electroactive portion; and
   (c) a binding entity reversibly immobilized on a solid surface within the component, said binding entity comprising:
      a first binding partner having specific binding activity for the chemical moiety, wherein binding of the first binding partner to the chemical moiety directly modulates an electrochemical property of the electroactive portion in a detectable manner; and
      a second binding partner, different from the first binding partner, selected such that the binding entity is released from the solid surface in the presence of analyte in a liquid medium.

2. The detection component of claim 1, wherein the electrically conducting solid support comprises gold, platinum, a metal oxide, carbon/graphite, silicon or silicate.

3. The detection component of claim 1, wherein binding of the first binding partner to the chemical moiety results in oxidation or reduction of the chemical moiety.

4. The detection component of claim 1, wherein the electroactive portion comprises an immunogen or a hapten, and wherein the first binding partner comprises an immunglobulin or an effective antigen-binding portion thereof having specific binding affinity for the chemical moiety.

5. The detection component of claim 4, wherein the immunoglobulin or effective antigen-binding portion thereof has specific binding affinity for the electroactive portion of the chemical moiety.

6. The detection component of claim 1, wherein the chemical moiety further comprises a conjugated system of delocalized electrons.

7. The detection component of claim 1, wherein the electroactive portion of the chemical moiety comprises an organometallic compound or a heteroaromatic compound.

8. The detection component of claim 1, wherein the electroactive portion of the chemical moiety comprises a monomer, dimer or polymer comprising one or more types of residues selected from among carbazoles, ferrocenes, pyrroles, furans, and thiophenes.

9. The detection component of claim 1, wherein the chemical moiety further comprises a pendant chain portion located between the electrically conducting solid support and the electroactive portion of the chemical moiety.

10. The detection component of claim 9, wherein the pendant chain portion comprises a conjugated system of delocalized electrons to facilitate transport of electrons between the electroactive portion and the solid support.

11. The detection component of claim 9, wherein the pendant chain portion is a substituted or unsubstituted alkyl or alkenyl group.

12. The detection component of claim 9, wherein the pendant chain portion has the formula $-(CH_2)_n-$, wherein n is an integer from 3 to 14.

13. The detection component of claim 9, wherein the pendant chain portion has the formula $-(CH_2)_n-$, wherein n is an integer from 5 to 12.

14. The detection component of claim 1, wherein the chemical moiety is a molecule which can form a self-assembling monolayer on the electrically conducting solid support.

15. The detection component of claim 1, wherein the solid surface on which the binding entity is reversibly immobilized is part of the electrically conducting solid support.

16. The detection component of claim 1, wherein the solid surface on which the binding entity is reversibly immobilized is separate from the electrically conducting solid support.

17. The detection component of claim 1, wherein the second binding partner specifically binds to the analyte, and wherein the binding entity is reversibly immobilized through binding of the second binding partner to an analyte analog.

18. The detection component of claim 17, wherein the second binding partner has greater affinity for the analyte than for the analyte analog.

19. The detection component of claim 1, wherein the second binding partner is an analyte analog, and wherein the binding entity is reversibly immobilized through binding of the analyte analog to an immobilized analyte-specific binding agent.

20. The detection component of claim 19, wherein the immobilized analyte specific binding agent has greater affinity for the analyte than for the analyte analog.

21. An assay device for detection of an analyte of interest comprising:
   (a) a detection component comprising:
      (i) an electrically conducting solid support;
      (ii) a chemical moiety immobilized on the solid support, said chemical moiety comprising an electroactive portion; and
      (iii) a binding entity reversibly immobilized on a solid surface within the component, said binding entity comprising:
         a first binding partner having specific binding activity for the chemical moiety, wherein binding of the binding partner to the chemical moiety directly modulates an electrochemical property of the electroactive portion in a detectable manner; and
         a second binding partner, different from the first binding partner, selected such that the binding entity is released from the solid support in the presence of analyte in a liquid medium; and
   (b) one of more additional components selected from among sample receiving means for accepting a sample and bringing it into contact with the detection component, detection means for detecting the modulation in the electrochemical property of the electroactive portion of the chemical moiety, and data display means for displaying an assay result.

22. The assay device of claim 21, wherein the electrically conducting solid support comprises gold, platinum, a metal oxide, carbon/graphite, silicon or silicate.

23. The assay device of claim 21, wherein binding of the first binding partner to the chemical moiety results in oxidation or reduction of the chemical moiety.

24. The assay device of claim 21, wherein the electroactive portion comprises an immunogen or a hapten, and wherein the first binding partner comprises an immunglobulin or an effective antigen-binding portion thereof having specific binding affinity for the chemical moiety.

25. The assay device of claim 24, wherein the immunoglobulin or effective antigen-binding portion thereof has specific binding affinity for the electroactive portion of the chemical moiety.

26. The assay device of claim 21, wherein the chemical moiety further comprises a conjugated system of delocalized electrons.

27. The assay device of claim 21, wherein the electroactive portion of the chemical moiety comprises an organometallic compound or a heteroaromatic compound.

28. The assay device of claim 21, wherein the electroactive portion of the chemical moiety comprises a monomer, dimer or polymer comprising one or more types of residues selected from among carbazoles, ferrocenes, pyrroles, furans, and thiophenes.

29. The assay device of claim 21, wherein the chemical moiety further comprises a pendant chain portion located between the electrically conducting solid support and the electroactive portion of the chemical moiety.

30. The assay device of claim 29, wherein the pendant chain portion comprises a conjugated system of delocalized electrons to facilitate transport of electrons between the electroactive portion and the solid support.

31. The assay device of claim 29, wherein the pendant chain portion is a substituted or unsubstituted alkyl or alkenyl group.

32. The assay device of claim 29, wherein the pendant chain portion has the formula —$(CH_2)_n$—, wherein n is an integer from 3 to 14.

33. The assay device of claim 29, wherein the pendant chain portion has the formula —$(CH_2)_n$—, wherein n is an integer from 5 to 12.

34. The assay device of claim 21, wherein the chemical moiety is a molecule which can form a self-assembling monolayer on the electrically conducting solid support.

35. The assay device of claim 21, wherein the solid surface on which the binding entity is reversibly immobilized is part of the electrically conducting solid support.

36. The assay device of claim 21, wherein the solid surface on which the binding entity is reversibly immobilized is separate from the electrically conducting solid support.

37. The assay device of claim 21, wherein the second binding partner specifically binds to the analyte, and wherein the binding entity is reversibly immobilized through binding of the second binding partner to an analyte analog.

38. The assay device of claim 37, wherein the second binding partner has greater affinity for the analyte than for the analyte analog.

39. The assay device of claim 21, wherein the second binding partner is an analyte analog, and wherein the binding entity is reversibly immobilized through binding of the analyte analog to an immobilized analyte-specific binding agent.

40. The assay device of claim 39, wherein the immobilized analyte specific binding agent has greater affinity for the analyte than for the analyte analog.

41. A method for detecting an analyte comprising the steps of:
   (a) placing a liquid sample to be assayed for the presence of the analyte in contact with
      (i) an electrically conducting solid support having immobilized thereon a chemical moiety, said chemical moiety comprising an electroactive portion; and
      (ii) a binding entity, said binding entity comprising:
         a first binding partner having specific binding activity for the chemical moiety, wherein binding of the binding partner to the chemical moiety directly modulates an electrochemical property of the electroactive portion in a detectable manner, and
         a second binding partner, different from the first binding partner, said second binding partner being an analyte-specific binding agent or an analyte analog; and
   (b) detecting modulation of the electrochemical property of the electroactive portion, wherein such modulation occurs only in the presence of analyte.

42. The method of claim 41, wherein the electrically conducting solid support comprises gold, platinum, a metal oxide, carbon/graphite, silicon or silicate.

43. The method of claim 41, wherein binding of the first binding partner to the chemical moiety results in oxidation or reduction of the chemical moiety.

44. The method of claim 41, wherein the electroactive portion comprises an immunogen or a hapten, and wherein the first binding partner comprises an immunglobulin or an effective antigen-binding portion thereof having specific binding affinity for the chemical moiety.

45. The method of claim 44, wherein the immunoglobulin or effective antigen-binding portion thereof has specific binding affinity for the electroactive portion of the chemical moiety.

46. The method of claim 41, wherein the chemical moiety further comprises a conjugated system of delocalized electrons.

47. The method of claim 41, wherein the electroactive portion of the chemical moiety comprises an organometallic compound or a heteroaromatic compound.

48. The method of claim 41, wherein the electroactive portion of the chemical moiety comprises a monomer, dimer or polymer comprising one or more types of residues selected from among carbazoles, ferrocenes, pyrroles, furans, and thiophenes.

49. The method of claim 41, wherein the chemical moiety further comprises a pendant chain portion located between the electrically conducting solid support and the electroactive portion of the chemical moiety.

50. The method of claim 49, wherein the pendant chain portion comprises a conjugated system of delocalized electrons to facilitate transport of electrons between the electroactive portion and the solid support.

51. The method of claim 49, wherein the pendant chain portion is a substituted or unsubstituted alkyl or alkenyl group.

52. The method of claim 49, wherein the pendant chain portion has the formula —$(CH_2)_n$—, wherein n is an integer from 3 to 14.

53. The method of claim 49, wherein the pendant chain portion has the formula —$(CH_2)_n$—, wherein n is an integer from 5 to 12.

54. The method of claim 41, wherein the chemical moiety is a molecule which can form a self-assembling monolayer on the electrically conducting solid support.

55. The method of claim 41, wherein the binding entity is reversibly immobilized on the electrically conducting solid support and is released from the solid support in the presence of analyte.

56. The method of claim 41, wherein the binding entity is reversibly immobilized on a solid surface separate from the electrically conducting solid support and is released from the solid surface in the presence of analyte.

57. The method of claim 41, wherein the second binding partner specifically binds to the analyte, and wherein the binding entity is reversibly immobilized to a solid surface through binding of the second binding partner to an analyte analog.

58. The method of claim 57, wherein the second binding partner has greater affinity for the analyte than for the analyte analog.

59. The method of claim 41, wherein the second binding partner is an analyte analog, and wherein the binding entity is reversibly immobilized to a solid surface through binding of the analyte analog to an immobilized analyte-specific binding agent.

60. The method of claim 59, wherein the immobilized analyte-specific binding agent has greater affinity for the analyte than for the analyte analog.

* * * * *

SEQUENCE LISTING

<160> NUMBER OF SEQ ID NOS: 15

<210> SEQ ID NO 1
<211> LENGTH: 804
<212> TYPE: DNA
<213> ORGANISM: artificial
<220> FEATURE:
<223> OTHER INFORMATION: anti-E3G antibody fragment

<400> SEQUENCE: 1

```
caggtgcagc tgcaggagtc tgggggtggc ttggtgaacc ttggagggtc tatgactctc      60
tcctgtgtag cctctggatt cactttcaat acctattaca tgtcttgggt tcgccagact     120
ccagagaaga cgctggagtt ggtcgcagcc attaatagtg atggtgaacc tatctattat     180
ccagacactt tgaagggccg agtcaccatc tctcgagaca atgccaagaa gaccctatac     240
ctgcaaatga gcagtctaaa ctttgaggac acagccttat attactgtgc aagacttact     300
tacgccgtgt atggtatgga ctattgggc caagggacca cggtcaccgt ctcctcaggt      360
ggaggcggtt caggcggagg tggctctggc ggtggcggat cggacatcga gctcacccaa     420
actccaccct ccctgcctgt cagtcttgga gatcaggttt ccatctcttg cagatctagt     480
cagagccttg tgtccaataa tagaaggaac tatttacatt ggtacctgca gaagccaggc     540
cagtctccaa agctcgtgat ctacaaagtt tccaaccgat tttctggggt cccagacagg     600
ttcagtggca gtggatcagg gacagatttc acactcaaga tcagcagagt ggcggctgag     660
gatctgggac tttatttctg ctctcaaagt tcacatgttc cgctcacgtt cggttctggg     720
accaagctcg agatcaaacg gggatctcat caccatcacc atcacggatc cggtagcggg     780
aactccggta agggtacct gaag                                             804
```

<210> SEQ ID NO 2
<211> LENGTH: 268
<212> TYPE: PRT
<213> ORGANISM: artificial
<220> FEATURE:
<223> OTHER INFORMATION: anti-E3G antibody fragment

<400> SEQUENCE: 2

```
Gln Val Gln Leu Gln Glu Ser Gly Gly Gly Leu Val Asn Leu Gly Gly
1               5                   10                  15

Ser Met Thr Leu Ser Cys Val Ala Ser Gly Phe Thr Phe Asn Thr Tyr
            20                  25                  30

Tyr Met Ser Trp Val Arg Gln Thr Pro Glu Lys Thr Leu Glu Leu Val
        35                  40                  45

Ala Ala Ile Asn Ser Asp Gly Glu Pro Ile Tyr Tyr Pro Asp Thr Leu
    50                  55                  60

Lys Gly Arg Val Thr Ile Ser Arg Asp Asn Ala Lys Lys Thr Leu Tyr
65                  70                  75                  80
```

```
Leu Gln Met Ser Ser Leu Asn Phe Glu Asp Thr Ala Leu Tyr Tyr Cys
                 85                  90                  95
Ala Arg Leu Thr Tyr Ala Val Tyr Gly Met Asp Tyr Trp Gly Gln Gly
            100                 105                 110
Thr Thr Val Thr Val Ser Ser Gly Gly Gly Ser Gly Gly Gly Gly
            115                 120                 125
Ser Gly Gly Gly Gly Ser Asp Ile Glu Leu Thr Gln Thr Pro Pro Ser
    130                 135                 140
Leu Pro Val Ser Leu Gly Asp Gln Val Ser Ile Ser Cys Arg Ser Ser
145                 150                 155                 160
Gln Ser Leu Val Ser Asn Asn Arg Arg Asn Tyr Leu His Trp Tyr Leu
                165                 170                 175
Gln Lys Pro Gly Gln Ser Pro Lys Leu Val Ile Tyr Lys Val Ser Asn
            180                 185                 190
Arg Phe Ser Gly Val Pro Asp Arg Phe Ser Gly Ser Gly Ser Gly Thr
            195                 200                 205
Asp Phe Thr Leu Lys Ile Ser Arg Val Ala Ala Glu Asp Leu Gly Leu
            210                 215                 220
Tyr Phe Cys Ser Gln Ser Ser His Val Pro Leu Thr Phe Gly Ser Gly
225                 230                 235                 240
Thr Lys Leu Glu Ile Lys Arg Gly Ser His His His His His His Gly
                245                 250                 255
Ser Gly Ser Gly Asn Ser Gly Lys Gly Tyr Leu Lys
            260                 265

<210> SEQ ID NO 3
<211> LENGTH: 22
<212> TYPE: DNA
<213> ORGANISM: artificial
<220> FEATURE:
<223> OTHER INFORMATION: primer

<400> SEQUENCE: 3
aggtsmarct gcagsagtcw gg                                              22

<210> SEQ ID NO 4
<211> LENGTH: 53
<212> TYPE: DNA
<213> ORGANISM: artificial
<220> FEATURE:
<223> OTHER INFORMATION: primer

<400> SEQUENCE: 4
aacagttaag cttccgcttg cggccgcgga gctggggtct tcgctgtggt gcg           53

<210> SEQ ID NO 5
<211> LENGTH: 53
<212> TYPE: DNA
<213> ORGANISM: artificial
<220> FEATURE:
<223> OTHER INFORMATION: primer

<400> SEQUENCE: 5
aacagttaag cttccgcttg cggccgctgg ttgtggtttt ggtgtcttgg gtt           53

<210> SEQ ID NO 6
<211> LENGTH: 378
<212> TYPE: DNA
<213> ORGANISM: artificial
<220> FEATURE:
```

-continued

<223> OTHER INFORMATION: anti-carbazole HC-V fragments

<400> SEQUENCE: 6

```
caggtgcagc tgcaggagtc aggggggagga ttggtgcagc ctgggggctc tctgagactc    60
tcctgtgcag cttctggact cacattgact acctattcaa cgggctggtt ccgccaggct    120
ccagggaagg agcgtgaatt tgtaggaatg cttggatgga gtggtggtgg caacacgtac    180
tacgcagact ccgtgaaggg ccgatttacc atctccagag acaacgccaa gaatatggtg    240
tttctgcaaa tgagcagcct gaaacctgag gacacggccg tttattactg tgcagcacga    300
caaccctacc gaggtagtta cagtgatccg aataattatc attactgggg ccaggggacc    360
caggtcaccg tctcctca                                                   378
```

<210> SEQ ID NO 7
<211> LENGTH: 126
<212> TYPE: PRT
<213> ORGANISM: artificial
<220> FEATURE:
<223> OTHER INFORMATION: anti-carbazole HC-V fragments

<400> SEQUENCE: 7

```
Gln Val Gln Leu Gln Glu Ser Gly Gly Leu Val Gln Pro Gly Gly
 1               5                  10                  15
Ser Leu Arg Leu Ser Cys Ala Ala Ser Gly Leu Thr Leu Thr Thr Tyr
            20                  25                  30
Ser Thr Gly Trp Phe Arg Gln Ala Pro Gly Lys Glu Arg Glu Phe Val
        35                  40                  45
Gly Met Leu Gly Trp Ser Gly Gly Gly Asn Thr Tyr Tyr Ala Asp Ser
    50                  55                  60
Val Lys Gly Arg Phe Thr Ile Ser Arg Asp Asn Ala Lys Asn Met Val
65                  70                  75                  80
Phe Leu Gln Met Ser Ser Leu Lys Pro Glu Asp Thr Ala Val Tyr Tyr
                85                  90                  95
Cys Ala Ala Arg Gln Pro Tyr Arg Gly Ser Tyr Ser Asp Pro Asn Asn
            100                 105                 110
Tyr His Tyr Trp Gly Gln Gly Thr Gln Val Thr Val Ser Ser
        115                 120                 125
```

<210> SEQ ID NO 8
<211> LENGTH: 375
<212> TYPE: DNA
<213> ORGANISM: artificial
<220> FEATURE:
<223> OTHER INFORMATION: anti-carbazole HC-V fragments

<400> SEQUENCE: 8

```
caggtgcagc tgcaggagtc aggggggagga ttggtgcagg ctgggggctc tctgagactc    60
tcctgtgcag cctctggacg caccttcagt gtttatgccg tgggttggtt ccgccaggct    120
ccagggaagg agcgtgagtt tgtaggatac tttggcacgc gtggtggaag aacatactat    180
gcagactccg tgaagggccg attcaccatc gccatagaca cgctaagaa cacggtgtat    240
ctgcaaatga atagcctgaa actagacgat acggccgttt attactgcgc agtccgtatg    300
ccgtatagtg gtgattaccg atctagtggg acatatgact actggggcca ggggacccag    360
gtcaccgtct cctca                                                      375
```

<210> SEQ ID NO 9
<211> LENGTH: 125

<212> TYPE: PRT
<213> ORGANISM: artificial
<220> FEATURE:
<223> OTHER INFORMATION: anti-carbazole HC-V fragments

<400> SEQUENCE: 9

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Val Tyr
            20                  25                  30

Ala Val Gly Trp Phe Arg Gln Ala Pro Gly Lys Glu Arg Glu Phe Val
        35                  40                  45

Gly Tyr Phe Gly Thr Arg Gly Gly Arg Thr Tyr Tyr Ala Asp Ser Val
    50                  55                  60

Lys Gly Arg Phe Thr Ile Ala Ile Asp Asn Ala Lys Asn Thr Val Tyr
65                  70                  75                  80

Leu Gln Met Asn Ser Leu Lys Leu Asp Asp Thr Ala Val Tyr Tyr Cys
                85                  90                  95

Ala Val Arg Met Pro Tyr Ser Gly Asp Tyr Arg Ser Ser Gly Thr Tyr
            100                 105                 110

Asp Tyr Trp Gly Gln Gly Thr Gln Val Thr Val Ser Ser
        115                 120                 125
```

<210> SEQ ID NO 10
<211> LENGTH: 147
<212> TYPE: PRT
<213> ORGANISM: artificial
<220> FEATURE:
<223> OTHER INFORMATION: amino acid sequence of the expression products of pPIC.HCV3-HIS2t

<400> SEQUENCE: 10

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Leu Thr Leu Thr Thr Tyr
            20                  25                  30

Ser Thr Gly Trp Phe Arg Gln Ala Pro Gly Lys Glu Arg Glu Phe Val
        35                  40                  45

Gly Met Leu Gly Trp Ser Gly Gly Asn Thr Tyr Tyr Ala Asp Ser
    50                  55                  60

Val Lys Gly Arg Phe Thr Ile Ser Arg Asp Asn Ala Lys Asn Met Val
65                  70                  75                  80

Phe Leu Gln Met Ser Ser Leu Lys Pro Glu Asp Thr Ala Val Tyr Tyr
                85                  90                  95

Cys Ala Ala Arg Gln Pro Tyr Arg Gly Ser Tyr Ser Asp Pro Asn Asn
            100                 105                 110

Tyr His Tyr Trp Gly Gln Gly Thr Gln Val Thr Val Ser Ser Gly Ser
        115                 120                 125

His His His His His His Gly Ser Gly Ser Gly Asn Ser Gly Lys Gly
    130                 135                 140

Tyr Leu Lys
145
```

<210> SEQ ID NO 11
<211> LENGTH: 146
<212> TYPE: PRT
<213> ORGANISM: artificial
<220> FEATURE:

<223> OTHER INFORMATION: amino acid sequence of the expression products
of pPIC.HCV4-HIS2t

<400> SEQUENCE: 11

```
Gln Val Gln Leu Gln Glu Ser Gly Gly Gly Leu Val Gln Ala Gly Gly
 1               5                  10                  15
Ser Leu Arg Leu Ser Cys Ala Ala Ser Gly Arg Thr Phe Ser Val Tyr
            20                  25                  30
Ala Val Gly Trp Phe Arg Gln Ala Pro Gly Lys Glu Arg Glu Phe Val
        35                  40                  45
Gly Tyr Phe Gly Thr Arg Gly Gly Arg Thr Tyr Tyr Ala Asp Ser Val
    50                  55                  60
Lys Gly Arg Phe Thr Ile Ala Ile Asp Asn Ala Lys Asn Thr Val Tyr
65                  70                  75                  80
Leu Gln Met Asn Ser Leu Lys Leu Asp Asp Thr Ala Val Tyr Tyr Cys
                85                  90                  95
Ala Val Arg Met Pro Tyr Ser Gly Asp Tyr Arg Ser Ser Gly Thr Tyr
            100                 105                 110
Asp Tyr Trp Gly Gln Gly Thr Gln Val Thr Val Ser Ser Gly Ser His
        115                 120                 125
His His His His Gly Ser Gly Ser Gly Ala Ser Gly Lys Gly Tyr
    130                 135                 140
Leu Lys
145
```

<210> SEQ ID NO 12
<211> LENGTH: 739
<212> TYPE: DNA
<213> ORGANISM: artificial
<220> FEATURE:
<223> OTHER INFORMATION: bispecific scFv4155-HCV3 and HCV24 construct

<400> SEQUENCE: 12

```
gaattcggcc gacatcgagc tcacccagtc tccagcctcc ctttctgcgt ctgtgggaga    60
aactgtcacc atcacatgtc gagcaagtgg gaatattcac aattatttag catggtatca   120
gcagaaacag ggaaaatctc ctcagctcct ggtctattat acaacaacct agcagatgg    180
tgtgccatca aggttcagtg gcagtggatc aggaacacaa tattctctca agatcaacag   240
cctgcaacct gaagattttg ggagttatta ctgtcaacat ttttggagta ctcctcggac   300
gttcggtgga accaagctcg agatcaaacg gggtggaggc ggttcaggcg gaggtggctc   360
tggcggtggc ggatcgcagg tgcagctgca ggagtcagga cctggcctgg tggcgccctc   420
acagagcctg tccatcacat gcaccgtctc agggttctca ttaaccggct atggtgtaaa   480
ctgggttcgc cagcctccag gaaagggtct ggagtggctg gaatgatttt ggggtgatgg   540
aaacacagac tataattcag ctctcaaatc cagactgagc atcagcaagg acaactccaa   600
gagccaagtt ttcttaaaaa tgaacagtct gcacactgat gacacagcca ggtactactg   660
tgccagagag agagattata ggcttgacta ctggggcgaa ggcaccacgg tcaccgtctc   720
ctcatgataa gcttgtcac                                                739
```

<210> SEQ ID NO 13
<211> LENGTH: 241
<212> TYPE: PRT
<213> ORGANISM: artificial
<220> FEATURE:
<223> OTHER INFORMATION: bispecific scFv4155-HCV3 and HCV24 construct

```
<400> SEQUENCE: 13

Asn Ser Ala Asp Ile Glu Leu Thr Gln Ser Pro Ala Ser Leu Ser Ala
1               5                   10                  15

Ser Val Gly Glu Thr Val Thr Ile Thr Cys Arg Ala Ser Gly Asn Ile
            20                  25                  30

His Asn Tyr Leu Ala Trp Tyr Gln Gln Lys Gln Gly Lys Ser Pro Gln
        35                  40                  45

Leu Leu Val Tyr Tyr Thr Thr Thr Leu Ala Asp Gly Val Pro Ser Arg
    50                  55                  60

Phe Ser Gly Ser Gly Ser Gly Thr Gln Tyr Ser Leu Lys Ile Asn Ser
65                  70                  75                  80

Leu Gln Pro Glu Asp Phe Gly Ser Tyr Tyr Cys Gln His Phe Trp Ser
                85                  90                  95

Thr Pro Arg Thr Phe Gly Gly Thr Lys Leu Glu Ile Lys Arg Gly Gly
            100                 105                 110

Gly Gly Ser Gly Gly Gly Gly Ser Gly Gly Gly Gly Ser Gln Val Gln
            115                 120                 125

Leu Gln Glu Ser Gly Pro Gly Leu Val Ala Pro Ser Gln Ser Leu Ser
    130                 135                 140

Ile Thr Cys Thr Val Ser Gly Phe Ser Leu Thr Gly Thr Gly Val Asn
145                 150                 155                 160

Trp Val Arg Gln Pro Pro Gly Lys Gly Leu Glu Trp Leu Gly Met Ile
                165                 170                 175

Trp Gly Asp Gly Asn Thr Asp Tyr Asn Ser Ala Leu Lys Ser Arg Leu
            180                 185                 190

Ser Ile Ser Lys Asp Asn Ser Lys Ser Gln Val Phe Leu Lys Met Asn
        195                 200                 205

Ser Leu His Thr Asp Asp Thr Ala Arg Tyr Tyr Cys Ala Arg Glu Arg
    210                 215                 220

Asp Tyr Arg Leu Asp Tyr Trp Gly Glu Gly Thr Thr Val Thr Val Ser
225                 230                 235                 240

Ser

<210> SEQ ID NO 14
<211> LENGTH: 409
<212> TYPE: PRT
<213> ORGANISM: artificial
<220> FEATURE:
<223> OTHER INFORMATION: expression product of pPIC.scFv4
      155-link-HCV3.HIS2t

<400> SEQUENCE: 14

Gln Val Gln Leu Gln Glu Ser Gly Gly Gly Leu Val Asn Leu Gly Gly
1               5                   10                  15

Ser Met Thr Leu Ser Cys Val Ala Ser Gly Phe Thr Phe Asn Thr Tyr
            20                  25                  30

Tyr Met Ser Trp Val Arg Gln Thr Pro Glu Lys Thr Leu Glu Leu Val
        35                  40                  45

Ala Ala Ile Asn Ser Asp Gly Glu Pro Ile Tyr Tyr Pro Asp Thr Leu
    50                  55                  60

Lys Gly Arg Val Thr Ile Ser Arg Asp Asn Ala Lys Lys Thr Leu Tyr
65                  70                  75                  80

Leu Gln Met Ser Ser Leu Asn Phe Glu Asp Thr Ala Leu Tyr Tyr Cys
                85                  90                  95
```

Ala Arg Leu Thr Tyr Ala Val Tyr Gly Met Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Ser Asp Ile Glu Leu Thr Gln Thr Pro Pro Ser
    130                 135                 140

Leu Pro Val Ser Leu Gly Asp Gln Val Ser Ile Ser Cys Arg Ser Ser
145                 150                 155                 160

Gln Ser Leu Val Ser Asn Asn Arg Arg Asn Tyr Leu His Trp Tyr Leu
                165                 170                 175

Gln Lys Pro Gly Gln Ser Pro Lys Leu Val Ile Tyr Lys Val Ser Asn
            180                 185                 190

Arg Phe Ser Gly Val Pro Asp Arg Phe Ser Gly Ser Gly Ser Gly Thr
            195                 200                 205

Asp Phe Thr Leu Lys Ile Ser Arg Val Ala Ala Glu Asp Leu Gly Leu
            210                 215                 220

Tyr Phe Cys Ser Gln Ser Ser His Val Pro Leu Thr Phe Gly Ser Gly
225                 230                 235                 240

Thr Lys Leu Glu Ile Lys Arg Gly Gly Gly Gly Ser Gly Gly Gly Gly
                245                 250                 255

Ser Gly Gly Gly Gly Ser Gln Val Gln Leu Gln Glu Ser Gly Gly Gly
            260                 265                 270

Leu Val Gln Pro Gly Gly Ser Leu Arg Leu Ser Cys Ala Ala Ser Gly
            275                 280                 285

Leu Thr Leu Thr Thr Tyr Ser Thr Gly Trp Phe Arg Gln Ala Pro Gly
            290                 295                 300

Lys Glu Arg Glu Phe Val Gly Met Leu Gly Trp Ser Gly Gly Gly Asn
305                 310                 315                 320

Thr Tyr Tyr Ala Asp Ser Val Lys Gly Arg Phe Thr Ile Ser Arg Asp
                325                 330                 335

Asn Ala Lys Asn Met Val Phe Leu Gln Met Ser Ser Leu Lys Pro Glu
            340                 345                 350

Asp Thr Ala Val Tyr Tyr Cys Ala Ala Arg Gln Pro Tyr Arg Gly Ser
            355                 360                 365

Tyr Ser Asp Pro Asn Asn Tyr His Tyr Trp Gly Gln Gly Thr Gln Val
        370                 375                 380

Thr Val Ser Ser Gly Ser His His His His His Gly Ser Gly Ser
385                 390                 395                 400

Gly Asn Ser Gly Lys Gly Tyr Leu Lys
                405

<210> SEQ ID NO 15
<211> LENGTH: 408
<212> TYPE: PRT
<213> ORGANISM: artificial
<220> FEATURE:
<223> OTHER INFORMATION: expression product of
      pPIC.scFv4155-link-HCV4.HIS2t

<400> SEQUENCE: 15

Gln Val Gln Leu Gln Glu Ser Gly Gly Gly Leu Val Asn Leu Gly Gly
1               5                   10                  15

Ser Met Thr Leu Ser Cys Val Ala Ser Gly Phe Thr Phe Asn Thr Tyr
            20                  25                  30

```
Tyr Met Ser Trp Val Arg Gln Thr Pro Glu Lys Thr Leu Glu Leu Val
         35                  40                  45
Ala Ala Ile Asn Ser Asp Gly Glu Pro Ile Tyr Tyr Pro Asp Thr Leu
 50                  55                  60
Lys Gly Arg Val Thr Ile Ser Arg Asp Asn Ala Lys Lys Thr Leu Tyr
 65                  70                  75                  80
Leu Gln Met Ser Ser Leu Asn Phe Glu Asp Thr Ala Leu Tyr Tyr Cys
             85                  90                  95
Ala Arg Leu Thr Tyr Ala Val Tyr Gly Met Asp Tyr Trp Gly Gln Gly
            100                 105                 110
Thr Thr Val Thr Val Ser Ser Gly Gly Gly Ser Gly Gly Gly Gly
            115                 120                 125
Ser Gly Gly Gly Gly Ser Asp Ile Glu Leu Thr Gln Thr Pro Pro Ser
130                 135                 140
Leu Pro Val Ser Leu Gly Asp Gln Val Ser Ile Ser Cys Arg Ser Ser
145                 150                 155                 160
Gln Ser Leu Val Ser Asn Asn Arg Arg Asn Tyr Leu His Trp Tyr Leu
                165                 170                 175
Gln Lys Pro Gly Gln Ser Pro Lys Leu Val Ile Tyr Lys Val Ser Asn
            180                 185                 190
Arg Phe Ser Gly Val Pro Asp Arg Phe Ser Gly Ser Gly Ser Gly Thr
        195                 200                 205
Asp Phe Thr Leu Lys Ile Ser Arg Val Ala Ala Glu Asp Leu Gly Leu
            210                 215                 220
Tyr Phe Cys Ser Gln Ser Ser His Val Pro Leu Thr Phe Gly Ser Gly
225                 230                 235                 240
Thr Lys Leu Glu Ile Lys Arg Gly Gly Gly Gly Ser Gly Gly Gly Gly
                245                 250                 255
Ser Gly Gly Gly Gly Ser Gln Val Gln Leu Gln Gln Ser Gly Gly Gly
            260                 265                 270
Leu Val Gln Ala Gly Gly Ser Leu Arg Leu Ser Cys Ala Ala Ser Gly
        275                 280                 285
Arg Thr Phe Ser Val Tyr Ala Val Gly Trp Phe Arg Gln Ala Pro Gly
290                 295                 300
Lys Gln Arg Glu Phe Val Gly Tyr Phe Gly Thr Arg Gly Gly Arg Thr
305                 310                 315                 320
Tyr Tyr Ala Asp Ser Val Lys Gly Arg Phe Thr Ile Ala Ile Asp Asn
                325                 330                 335
Ala Lys Asn Thr Val Tyr Leu Gln Met Asn Ser Leu Lys Leu Asp Asp
            340                 345                 350
Thr Ala Val Tyr Tyr Cys Ala Val Arg Met Pro Tyr Ser Gly Asp Tyr
        355                 360                 365
Arg Ser Ser Gly Thr Tyr Asp Tyr Trp Gly Gln Gly Thr Gln Val Thr
    370                 375                 380
Val Ser Ser Gly Ser His His His His His Gly Ser Gly Ser Gly
385                 390                 395                 400
Asn Ser Gly Lys Gly Tyr Leu Lys
                405
```